United States Patent
Yoshida et al.

(10) Patent No.: US 6,630,616 B1
(45) Date of Patent: Oct. 7, 2003

(54) ARABIDOPSIS MPC1 GENE AND METHODS FOR CONTROLLING FLOWERING TIME

(75) Inventors: Nobumasa Yoshida, Chiba (JP); Yukihiro Yanai, Chiba (JP); Yoshihiro Kato, Chiba (JP); Junzo Hiratsuka, Chiba (JP); Shigeru Takahashi, Chiba (JP); Tatsushi Miwa, Tokyo (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/339,947

(22) Filed: Jun. 25, 1999

(30) Foreign Application Priority Data

Jun. 26, 1998 (JP) ............................................ 10-180065
Jun. 24, 1999 (JP) ............................................ 11-179043

(51) Int. Cl.$^7$ .......................... C12N 15/29; C12N 5/04; C12N 15/82; C12N 15/90; A01H 5/00
(52) U.S. Cl. .................... 800/290; 435/320.1; 435/419; 435/468; 536/23.6; 800/286; 800/298
(58) Field of Search ............................ 435/320.1, 69.1, 435/410, 419, 455, 468, 471; 536/23.6; 800/278, 285, 286, 295, 298, 90

(56) References Cited

FOREIGN PATENT DOCUMENTS

| WO | WO96/38560 A2 | 12/1996 | |
|---|---|---|---|
| WO | WO97/10339 A1 | 3/1997 | |
| WO | WO97/49811 | * 12/1997 | ........... C12N/15/29 |

OTHER PUBLICATIONS

Takatsuji et al, Zinc–finger proteins: the classical zinc finger emerges in contemporary plant science, 1999, Plant Molecular Biology, vol. 39, pp. 1073–1078.*

Fisher et al, A structurally Novel Transferrin–like . . . Grown in High Salinities, 1997, The Journal of Biological Chemistry, vol. 272 No. 3, pp. 1566–1570.*

Aukeman, M. J. and Amasino, R. M. "Molecular genetic analysis of flowering time in Arabidopsis." 1996, Cell & Developmental Biology, vol. 7, pp. 427–433.*

I. Lee et al, "Isolation of luminidependens: A gene involved in the control of flowering time in arabidopsis", The Plant Cell, vol. 6, pp. 75–83, Jan. 1994.

Medline Abstract of Development Nov. 1997; 124(22):4481–91.

Medline Abstract of Development Sep. 1997; 124(17):3343–51.

Medline Abstract of Curr Biol Aug. 1, 1997;7(8):581–7.

Medline Abstract of Science Jan. 3, 1997;275(5296):80–3.

Medline Abstract of Development May 1996; 122(5):1535–44.

Medline Abstract of Plant Cell Aug. 1995; 7(8):1249–58.

Medline Abstract of Plant Mol Biol Jul. 1995; 28(4):723–37.

Medline Abstract of Plant Cell May 1995; 7(5):517–27.

Medline Abstract of Plant Mol Biol Jan. 1995; 27(1):69–78.

Medline Abstract of Biochim Biophys Acta Sep. 13, 1994; 1219(1):201–4.

Medline Abstract of Plant Cell Sep. 1994; 6(9):1211–25.

Yang et al, "Genetic Regulation of Shoot Development in Arabidopsis: Role of the EMF Genes", Development Biology, 169, 421–435 (1995).

Sung et al, "EMF, an Arabidopsis Gene Required for Vegetative Shoot Development", Science, 258, 1645–1647 (1992).

Kunkel, "Rapid and Efficient Site–Specific Mutagenesis Without Phenotypic Selection", Proc. Natl. Acad. Sci. USA, 82, 488–492 (1985).

Southern, "Detection of Specific Sequences Among DNA Fragments Separated by Gel Electrophoresis", J. Mol. Biol., 98, 503–517 (1975).

Odell et al, "Identification of DNA Sequences Required for Activity of the Cauliflower Mosaic Virus 35S Promoter", Nature, 313, 810–812 (1985).

Zhang et al, "Analysis of Rice Act1 5' Region Activity in Transgenic Rice Plant", The Plant Cell, 3, 1155–1165 (1991).

Xu et al, "Regulation, Expression and Function of a New Basic Chitinase Gene in Rice (*Oryza sativa* L.)", Plant Molecular Biology, 30, 387–401 (1996).

Ohshima et al, "Analysis of Stress–Induced or Salicylic Acid–Induced Expression of the Pathogenesis–Related 1a Protein Gene in Transgenic Tobacco", The Plant Cell, 2, 95–106 (1990).

Aguan et al, "Low–Temperature–Dependent Expression of a Rice Gene Encoding a Protein With a Leucine–Zipper Motif", Mol Gen Genet, 240, 1–8, (1993).

Yoshida et al, "Heat–Inducible Expression System for a Foreign Gene in Cultured Tobacco Cells Using the HSP18.2 Promoter of Arabidopsis Thaliana", Appl. Microbiol Biotechnol, 44, 466–472 (1995).

Yamaguchi–Shinozaki et al, "Four Tightly Linked Rab Genes are Differentially Expressed in Rice", Plant Molecular Biology, 14, 29–39 (1989).

Schulze–Lefert et al, "Inducible in vivo DNA Footprints Define Sequences Necessary for UV Light Activation of the Parsley Chalcone Synthase Gene", The EMBO Journal, 8(3), 651–656 (1989).

(List continued on next page.)

Primary Examiner—Ashwin Mehta
(74) Attorney, Agent, or Firm—Burns, Doane, Swecker & Mathis, LLP

(57) ABSTRACT

Flowering regulating genes of plants and methods for controlling plant flowering are provided. The flowering time can be modified in comparison with wild type plants by enhancing or inhibiting the expression of the flowering regulating gene. Transgenic plants in which the expression of the flowering regulating gene is regulated is also provided.

10 Claims, 1 Drawing Sheet

OTHER PUBLICATIONS

Walker et al, "DNA Sequences Required for Anaerobic Expresion of the Maize Alcohol Dehydrogenase 1 Gene", Proc. Natl. Acad. Sci. USA, 84, 6624–6628 (1987).

Fujimura et al, "Regeneration of Rice Plants from Protoplasts", Plant Tissue Culture Letters, 2(2), 74–75 (1985).

Shillito et al, "Regeneration of Fertile Plants from Protoplasts of Elite Inbred Maize", Bio/Technology, 7, 581–587 (1989).

Visser et al, "Efficient Transformation of Potato (*Solanum tuberosum*, L.) Using a Binary Vector in Agrobacterium rhizogenes", Theor Appl Genet, 78, 594–600 (1989).

Akama et al, "Efficient Transformation of *Arabidopsis thaliana*: Comparison of the Efficiencies with Various Organs, Plant Ecotypes and Agrobacterium Strains", Plant Cell Reports, 12, 7–11 (1992).

Gamborg et al, "Nutrient Requirements of Suspension Cultures in Soybean Root Cells", Experimenal Cell Research, 50, 151–158 (1968).

Liu et al, "Isolation and Mapping of a New Set of 129 RFLP Markers in *Arabidopsis thaliana* Using Recombinant Inbred Lines", The Plant Journal, 10(4), 733–736 (1996).

Konieczny et al, "A Procedure for Mapping Arabidopsis Mutations Using Co-Dominant Ecotype-Specific PCR-Based Markers", The Plant Journal, 4(2), 403–410 (1993).

Bell et al, "Assignment of 30 Microsatellite Loci to the Linkage Map of Arabidopsis", Genomics, 19, 137–144 (1994).

Lister et al, "RFLP Map Generated on Landsberg erecta x Columbia Recombinant Inbred Lines", (1995).

Smith et al, "Characterization and Mapping of Ds–GUS–T–DNA Lines for Targeted Insertional Mutagenesis", The Plant Journal, 10(4), 721–732 (1996).

Creusot et al, "The CIC Library: a Large Insert YAC Library for Genome Mapping in *Arabisopsis thaliana*", The Plant Journal, 8(5), 763–770 (1995).

Liu et al, "Generation of a High–Quality P1 Library of Arabidopsis Suitable for Chromosome Walking", The Plant Journal, 7(2), 351–358 (1995).

Newman et al, "Genes Galore: A Summary of Methods for Accessing Results from Large–Scale Partial Sequencing of Anonymous Arabidiopsis cDNA Clones", Plant Physiol., 106, 1241–1255 (1994).

Rosenfeld et al, "Zinc Fingers: Conserved Properties that Can Distinguish Between Spurious and Actual DNA–Binding Motifs", Journal of Biomolecular Structure & Dynamics, ISSN 0739–1102, 11(3), 557–570 (1993).

Jefferson et al, "GUS Fusions: β–glucuronidase as a Sensitive and Versatile Gene Fusion Marker in Higher Plants", The EMBO Journal, 6(13), 3901–3907 (1987).

Murashige et al, "A Revised Medium for Rapid Growth and Bio Assays with Tobacco Tissue Cultures", Physiologia Plantarum, 15, 473–497 (1962).

Tsunematsu et al, "Construction of an RFLP/RAPD Linkage Map by Using Recombinant Inbred Lines", Rice Genetics Newsletter, 10, 89–90. Dec., 1993.

Montgomery et al, "Double–Stranded RNA as a Mediator in Sequence–Specific Genetic Silencing and Co–Suppression", TIG, 14(7), 255–258 (1998).

Needleman et al, "A General Method Applicable to the Search for Similarities in the Amino Acid Sequence of Two Proteins", J. Mol. Biol., 48, 443–453 (1970).

Waterman, "Multiple Sequence Alignment by Consensus", Nucleic Acids Research, 14(22), 9095–9102 (1986).

Smith et al, "Single–Step Purification of Polypeptides Expressed in *Escherichia coli* as Fusions with Glutathione S–Transferase", Gene, 67, 31–40 (1988).

J. Putterill et al., "The Constans Gene of Arabidopsis Promotes Flowering and Encodes a Protein Showing Similarities to Zinc Finger Transcription Factors," Cell, vol. 80, 847–857, Mar. 24, 1995, by Cell Press, Cambridge, Massachusetts.

* cited by examiner

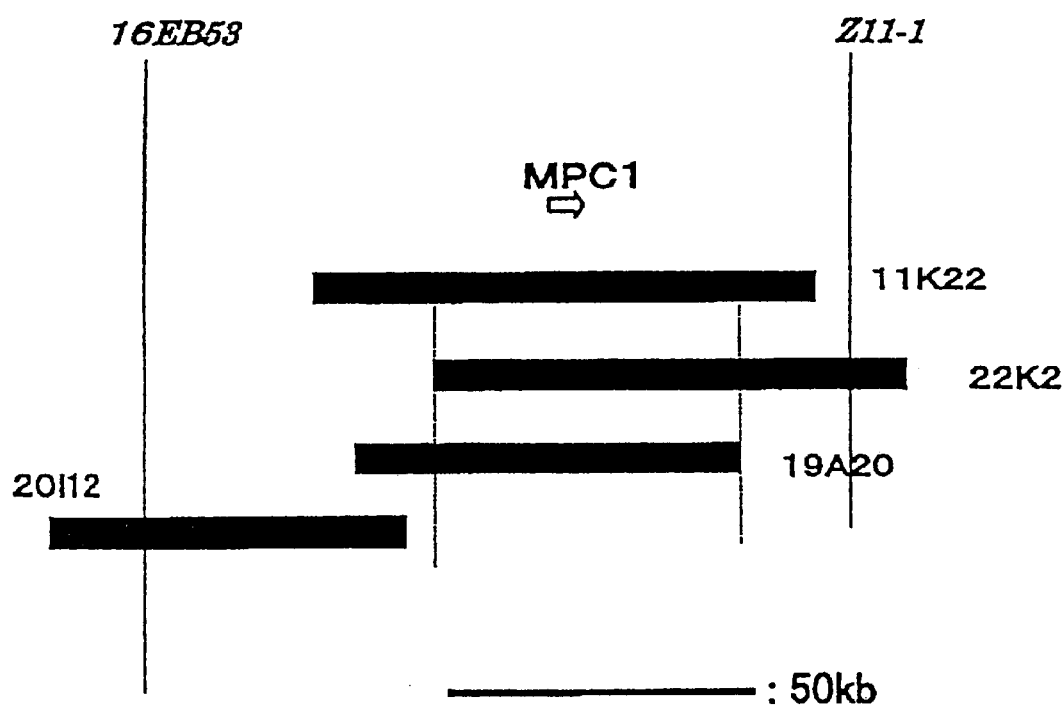

SEQUENCE LISTING

```
<160> NUMBER OF SEQ ID NOS:  20

<210> SEQ ID NO 1
<211> LENGTH: 611
<212> TYPE: PRT
<213> ORGANISM: Arabidopsis thaliana
<220> FEATURE:
<221> NAME/KEY: ZN_FING
<222> LOCATION: (306)..(327)

<400> SEQUENCE: 1

Met Cys His Glu Asp Ser Arg Leu Arg Ile Ser Glu Glu Glu Glu Ile
  1               5                  10                  15

Ala Ala Glu Glu Ser Leu Ala Ala Tyr Cys Lys Pro Val Glu Leu Tyr
             20                  25                  30

Asn Ile Ile Gln Arg Arg Ala Ile Arg Asn Pro Leu Phe Leu Gln Arg
         35                  40                  45

Cys Leu His Tyr Lys Ile Glu Ala Lys His Lys Arg Arg Ile Gln Met
     50                  55                  60

Thr Val Phe Leu Ser Gly Ala Ile Asp Ala Gly Val Gln Thr Gln Lys
 65                  70                  75                  80

Leu Phe Pro Leu Tyr Ile Leu Leu Ala Arg Leu Val Ser Pro Lys Pro
                 85                  90                  95

Val Ala Glu Tyr Ser Ala Val Tyr Arg Phe Ser Arg Ala Cys Ile Leu
            100                 105                 110

Thr Gly Gly Leu Gly Val Asp Gly Val Ser Gln Ala Gln Ala Asn Phe
        115                 120                 125

Leu Leu Pro Asp Met Asn Arg Leu Ala Leu Glu Ala Lys Ser Gly Ser
    130                 135                 140
```

```
Leu Ala Ile Leu Phe Ile Ser Phe Ala Gly Ala Gln Asn Ser Gln Phe
145                 150                 155                 160

Gly Ile Asp Ser Gly Lys Ile His Ser Gly Asn Ile Gly Gly His Cys
                165                 170                 175

Leu Trp Ser Lys Ile Pro Leu Gln Ser Leu Tyr Ala Ser Trp Gln Lys
                180                 185                 190

Ser Pro Asn Met Asp Leu Gly Gln Arg Val Asp Thr Val Ser Leu Val
            195                 200                 205

Glu Met Gln Pro Cys Phe Ile Lys Leu Lys Ser Met Ser Glu Glu Lys
        210                 215                 220

Cys Val Ser Ile Gln Val Pro Ser Asn Pro Leu Thr Ser Ser Ser Pro
225                 230                 235                 240

Gln Gln Val Gln Val Thr Ile Ser Ala Glu Val Gly Ser Thr Glu
                245                 250                 255

Lys Ser Pro Tyr Ser Ser Phe Ser Tyr Asn Asp Ile Ser Ser Ser Ser
            260                 265                 270

Leu Leu Gln Ile Ile Arg Leu Arg Thr Gly Asn Val Val Phe Asn Tyr
        275                 280                 285

Arg Tyr Tyr Asn Asn Lys Leu Gln Lys Thr Glu Val Thr Glu Asp Phe
        290                 295                 300

Ser Cys Pro Phe Cys Leu Val Lys Cys Ala Ser Phe Lys Gly Leu Arg
305                 310                 315                 320

Tyr His Leu Pro Ser Thr His Asp Leu Leu Asn Phe Glu Phe Trp Val
                325                 330                 335

Thr Glu Glu Phe Gln Ala Val Asn Val Ser Leu Lys Thr Glu Thr Met
            340                 345                 350

Ile Ser Lys Val Asn Glu Asp Val Asp Pro Lys Gln Gln Thr Phe
        355                 360                 365

Phe Phe Ser Ser Lys Lys Phe Arg Arg Arg Gln Lys Ser Gln Val
370                 375                 380

Arg Ser Ser Arg Gln Gly Pro His Leu Gly Leu Gly Cys Glu Val Leu
385                 390                 395                 400

Asp Lys Thr Asp Asp Ala His Ser Val Arg Ser Glu Lys Ser Arg Ile
            405                 410                 415

Pro Pro Gly Lys His Tyr Glu Arg Ile Gly Gly Ala Glu Ser Gly Gln
            420                 425                 430

Arg Val Pro Pro Gly Thr Ser Pro Ala Asp Val Gln Ser Cys Gly Asp
            435                 440                 445

Pro Asp Tyr Val Gln Ser Ile Ala Gly Ser Thr Met Leu Gln Phe Ala
    450                 455                 460

Lys Thr Arg Lys Ile Ser Ile Glu Arg Ser Asp Leu Arg Asn Arg Ser
465                 470                 475                 480

Leu Leu Gln Lys Arg Gln Phe Phe His Ser His Arg Ala Gln Pro Met
            485                 490                 495

Ala Leu Glu Gln Val Leu Ser Asp Arg Asp Ser Glu Asp Glu Val Asp
                500                 505                 510

Asp Asp Val Ala Asp Phe Glu Asp Arg Arg Met Leu Asp Asp Phe Val
        515                 520                 525

Asp Val Thr Lys Asp Glu Lys Gln Met Met His Met Trp Asn Ser Phe
        530                 535                 540

Val Arg Lys Gln Arg Val Leu Ala Asp Gly His Ile Pro Trp Ala Cys
545                 550                 555                 560

Glu Ala Phe Ser Arg Leu His Gly Pro Ile Met Val Arg Thr Pro His
```

```
                         565                 570                 575
Leu Ile Trp Cys Trp Arg Val Phe Met Val Lys Leu Trp Asn His Gly
                580                 585                 590

Leu Leu Asp Ala Arg Thr Met Asn Asn Cys Asn Thr Phe Leu Glu Gln
        595                 600                 605

Leu Gln Ile
    610

<210> SEQ ID NO 2
<211> LENGTH: 2280
<212> TYPE: DNA
<213> ORGANISM: Arabidopsis thaliana
<220> FEATURE:
<221> NAME/KEY: CDS
<222> LOCATION: (310)..(2142)
<221> NAME/KEY: misc_feature
<222> LOCATION: (1650)..(1655)
<223> OTHER INFORMATION: BamHI recognition site
<221> NAME/KEY: misc_feature
<222> LOCATION: (1984)..(1989)
<223> OTHER INFORMATION: SphI recognition site

<400> SEQUENCE: 2
aagataattt ctcacaatta gggttttttt tttcttctga gttaactgtt ccatctccat    60
cctaatcttc accttctcct tgatttcgag atctctgtca atttgttgaa tctgttcttt   120
atctaattag ctcaactccg agtctttgct ggattttgaa gcttttgtag ctgaagcaaa   180
tttgtaatct gtgatggtgt atgcactgat tctgggtatg gtattgtact ctaggatctc   240
gtagcgagaa tgccaggcat tcctcttgtt agtcgtgaaa cctcttcttg ttcaagaagc   300 acagagcag atg tgc cat gaa gac tcc cgt ctg cgt att tcg gaa gag gag     351
          Met Cys His Glu Asp Ser Arg Leu Arg Ile Ser Glu Glu Glu
            1               5                  10 gag att gct gct gaa gag agc ttg gct gcc tat tgc aag cct gtt gaa       399
Glu Ile Ala Ala Glu Glu Ser Leu Ala Ala Tyr Cys Lys Pro Val Glu
 15                  20                  25                  30 ctc tac aat atc att caa cgc cgt gct att agg aat ccc ttg ttt ctt       447
Leu Tyr Asn Ile Ile Gln Arg Arg Ala Ile Arg Asn Pro Leu Phe Leu
                 35                  40                  45 cag cga tgt ttg cat tat aag att gag gca aaa cat aaa agg aga ata       495
Gln Arg Cys Leu His Tyr Lys Ile Glu Ala Lys His Lys Arg Arg Ile
             50                  55                  60 caa atg act gta ttc ctc tcg ggc gct ata gat gct ggg gta caa act       543
Gln Met Thr Val Phe Leu Ser Gly Ala Ile Asp Ala Gly Val Gln Thr
         65                  70                  75 caa aaa tta ttc cct ctg tat att ttg ttg gca aga ctc gtt tct cct       591
Gln Lys Leu Phe Pro Leu Tyr Ile Leu Leu Ala Arg Leu Val Ser Pro
     80                  85                  90 aag cct gtc gct gag tat tct gca gta tat agg ttc agt cga gca tgt       639
Lys Pro Val Ala Glu Tyr Ser Ala Val Tyr Arg Phe Ser Arg Ala Cys
 95                 100                 105                 110 atc cta act ggt gga ttg ggg gtt gat gga gtt agt caa gcc caa gcc       687
Ile Leu Thr Gly Gly Leu Gly Val Asp Gly Val Ser Gln Ala Gln Ala
                115                 120                 125 aac ttt ctt ctc cct gat atg aat aga ctc gca ttg gag gca aaa tca       735
Asn Phe Leu Leu Pro Asp Met Asn Arg Leu Ala Leu Glu Ala Lys Ser
            130                 135                 140 gga tca ctc gct atc ttg ttt atc agc ttt gct ggt gcg caa aat tct       783
Gly Ser Leu Ala Ile Leu Phe Ile Ser Phe Ala Gly Ala Gln Asn Ser
        145                 150                 155 caa ttt ggc att gat tca ggc aag att cat tca gga aat ata gga gga       831
```

```
                                                         -continued

Gln Phe Gly Ile Asp Ser Gly Lys Ile His Ser Gly Asn Ile Gly Gly
    160                 165                 170 cat tgt tta tgg agc aaa ata cct ctg caa tca ctg tat gcg tcg tgg       879
His Cys Leu Trp Ser Lys Ile Pro Leu Gln Ser Leu Tyr Ala Ser Trp
175                 180                 185                 190 cag aaa tca cca aac atg gac ttg gga cag aga gta gac aca gtc tct       927
Gln Lys Ser Pro Asn Met Asp Leu Gly Gln Arg Val Asp Thr Val Ser
                    195                 200                 205 ctt gtt gaa atg cag cct tgc ttc ata aag cta aag tcc atg agt gag       975
Leu Val Glu Met Gln Pro Cys Phe Ile Lys Leu Lys Ser Met Ser Glu
                210                 215                 220 gaa aag tgt gtc tcg att cag gtg ccc agc aat cca ctc acc tcg agc      1023
Glu Lys Cys Val Ser Ile Gln Val Pro Ser Asn Pro Leu Thr Ser Ser
            225                 230                 235 tct ccg cag caa gtg caa gtc acc ata tct gca gaa gaa gtt ggg tca      1071
Ser Pro Gln Gln Val Gln Val Thr Ile Ser Ala Glu Glu Val Gly Ser
        240                 245                 250 acg gaa aaa tct cct tat agt tca ttt tca tat aat gac atc tct tcc      1119
Thr Glu Lys Ser Pro Tyr Ser Ser Phe Ser Tyr Asn Asp Ile Ser Ser
255                 260                 265                 270 tct tcc ttg ttg caa att atc agg ttg aga aca gga aat gta gtt ttc      1167
Ser Ser Leu Leu Gln Ile Ile Arg Leu Arg Thr Gly Asn Val Val Phe
                    275                 280                 285 aac tac aga tac tat aac aac aaa ttg cag aag act gaa gta act gaa      1215
Asn Tyr Arg Tyr Tyr Asn Asn Lys Leu Gln Lys Thr Glu Val Thr Glu
                290                 295                 300 gac ttt tct tgt cca ttc tgc tta gta aaa tgt gcc agt ttc aag ggc      1263
Asp Phe Ser Cys Pro Phe Cys Leu Val Lys Cys Ala Ser Phe Lys Gly
            305                 310                 315 ctg aga tat cac ttg cca tca acc cac gat ctc ctc aat ttc gag ttt      1311
Leu Arg Tyr His Leu Pro Ser Thr His Asp Leu Leu Asn Phe Glu Phe
        320                 325                 330 tgg gta act gaa gaa ttt cag gcg gta aat gtc tcc ctc aag act gag      1359
Trp Val Thr Glu Glu Phe Gln Ala Val Asn Val Ser Leu Lys Thr Glu
335                 340                 345                 350 aca atg ata tcc aag gtt aat gag gat gac gtt gac cca aag cag caa      1407
Thr Met Ile Ser Lys Val Asn Glu Asp Asp Val Asp Pro Lys Gln Gln
                    355                 360                 365 act ttc ttt ttt tct tcc aaa aaa ttc aga cgg agg agg caa aag agt      1455
Thr Phe Phe Phe Ser Ser Lys Lys Phe Arg Arg Arg Arg Gln Lys Ser
                370                 375                 380 cag gta cgg agc tca agg caa ggg cct cat ctt gga tta ggt tgc gag      1503
Gln Val Arg Ser Ser Arg Gln Gly Pro His Leu Gly Leu Gly Cys Glu
            385                 390                 395 gtg cta gat aag act gat gat gct cat tct gtt aga agt gag aag agc      1551
Val Leu Asp Lys Thr Asp Asp Ala His Ser Val Arg Ser Glu Lys Ser
        400                 405                 410 cga ata cca cct gga aag cat tac gaa aga att ggg ggt gct gag tct      1599
Arg Ile Pro Pro Gly Lys His Tyr Glu Arg Ile Gly Gly Ala Glu Ser
415                 420                 425                 430 ggt caa aga gtt cct cct ggc acg agt cct gca gac gtg caa tca tgt      1647
Gly Gln Arg Val Pro Pro Gly Thr Ser Pro Ala Asp Val Gln Ser Cys
                    435                 440                 445 ggg gat cca gat tat gtg cag tcg ata gct gga agt aca atg ttg cag      1695
Gly Asp Pro Asp Tyr Val Gln Ser Ile Ala Gly Ser Thr Met Leu Gln
                450                 455                 460 ttt gca aaa acg agg aaa ata tct ata gaa cgg tcg gac ttg agg aac      1743
Phe Ala Lys Thr Arg Lys Ile Ser Ile Glu Arg Ser Asp Leu Arg Asn
            465                 470                 475
```

```
cga agc ctc ctt cag aag aga cag ttc ttc cac tct cat cga gct cag      1791
Arg Ser Leu Leu Gln Lys Arg Gln Phe Phe His Ser His Arg Ala Gln
    480                 485                 490 ccc atg gct cta gaa caa gta ctt tcg gac cgg gat agt gaa gat gaa      1839
Pro Met Ala Leu Glu Gln Val Leu Ser Asp Arg Asp Ser Glu Asp Glu
495                 500                 505                 510 gtt gat gat gat gtg gca gat ttt gaa gat aga agg atg ctc gat gat      1887
Val Asp Asp Asp Val Ala Asp Phe Glu Asp Arg Arg Met Leu Asp Asp
                515                 520                 525 ttc gtt gat gtg act aaa gat gag aaa cag atg atg cac atg tgg aac      1935
Phe Val Asp Val Thr Lys Asp Glu Lys Gln Met Met His Met Trp Asn
        530                 535                 540 tcg ttt gtg agg aag cag cga gta tta gca gat ggt cac att cca tgg      1983
Ser Phe Val Arg Lys Gln Arg Val Leu Ala Asp Gly His Ile Pro Trp
    545                 550                 555 gca tgc gag gca ttc tca aga ttg cac gga ccc atc atg gtt cga aca      2031
Ala Cys Glu Ala Phe Ser Arg Leu His Gly Pro Ile Met Val Arg Thr
560                 565                 570 ccg cac ttg att tgg tgc tgg aga gtg ttt atg gtg aaa ctg tgg aac      2079
Pro His Leu Ile Trp Cys Trp Arg Val Phe Met Val Lys Leu Trp Asn
575                 580                 585                 590 cac ggt ctt ctt gat gcc cga acc atg aac aac tgt aat acc ttt ctc      2127
His Gly Leu Leu Asp Ala Arg Thr Met Asn Asn Cys Asn Thr Phe Leu
                595                 600                 605 gaa cag ctc caa att tgaaaaccca agaaatcatt aatttaagta gaaaaacaaa     2182
Glu Gln Leu Gln Ile
            610 gaaagacaag agaagaagag ttttgggttc tcatttaact acttttggtg ttttaagaga    2242 aagaggagca tatttatgca tgaaaaaaaa aaaaaaaa                            2280

<210> SEQ ID NO 3
<211> LENGTH: 5580
<212> TYPE: DNA
<213> ORGANISM: Arabidopsis thaliana
<220> FEATURE:
<221> NAME/KEY: intron
<222> LOCATION: (162)..(267)
<221> NAME/KEY: intron
<222> LOCATION: (394)..(565)
<221> NAME/KEY: CDS
<222> LOCATION: (588)..(713)
<221> NAME/KEY: intron
<222> LOCATION: (714)..(930)
<221> NAME/KEY: CDS
<222> LOCATION: (931)..(986)
<221> NAME/KEY: intron
<222> LOCATION: (987)..(1132)
<221> NAME/KEY: CDS
<222> LOCATION: (1133)..(1247)
<221> NAME/KEY: intron
<222> LOCATION: (1248)..(1344)
<221> NAME/KEY: CDS
<222> LOCATION: (1345)..(1504)
<221> NAME/KEY: intron
<222> LOCATION: (1505)..(1596)
<221> NAME/KEY: CDS
<222> LOCATION: (1597)..(1647)
<221> NAME/KEY: intron
<222> LOCATION: (1648)..(1854)
<221> NAME/KEY: CDS
<222> LOCATION: (1855)..(1994)
<221> NAME/KEY: intron
<222> LOCATION: (1995)..(2197)
<221> NAME/KEY: CDS
<222> LOCATION: (2198)..(2260)
<221> NAME/KEY: intron
<222> LOCATION: (2261)..(2350)
<221> NAME/KEY: CDS
```

```
<222> LOCATION: (2351)..(2472)
<221> NAME/KEY: intron
<222> LOCATION: (2473)..(2714)
<221> NAME/KEY: CDS
<222> LOCATION: (2715)..(2779)
<221> NAME/KEY: intron
<222> LOCATION: (2780)..(2870)
<221> NAME/KEY: CDS
<222> LOCATION: (2871)..(2930)
<221> NAME/KEY: intron
<222> LOCATION: (2931)..(3038)
<221> NAME/KEY: CDS
<222> LOCATION: (3039)..(3092)
<221> NAME/KEY: intron
<222> LOCATION: (3093)..(3174)
<221> NAME/KEY: CDS
<222> LOCATION: (3175)..(3234)
<221> NAME/KEY: intron
<222> LOCATION: (3235)..(3654)
<221> NAME/KEY: CDS
<222> LOCATION: (3656)..(3701)
<221> NAME/KEY: intron
<222> LOCATION: (3702)..(3784)
<221> NAME/KEY: CDS
<222> LOCATION: (3785)..(3885)
<221> NAME/KEY: intron
<222> LOCATION: (3886)..(4052)
<221> NAME/KEY: CDS
<222> LOCATION: (4053)..(4272)
<221> NAME/KEY: intron
<222> LOCATION: (4273)..(4428)
<221> NAME/KEY: CDS
<222> LOCATION: (4429)..(4477)
<221> NAME/KEY: intron
<222> LOCATION: (4478)..(4552)
<221> NAME/KEY: CDS
<222> LOCATION: (4553)..(4636)
<221> NAME/KEY: intron
<222> LOCATION: (4637)..(4982)
<221> NAME/KEY: CDS
<222> LOCATION: (4983)..(5062)
<221> NAME/KEY: intron
<222> LOCATION: (5063)..(5265)
<221> NAME/KEY: CDS
<222> LOCATION: (5266)..(5355)
<221> NAME/KEY: intron
<222> LOCATION: (5356)..(5445)
<221> NAME/KEY: CDS
<222> LOCATION: (5446)..(5542)

<400> SEQUENCE: 3
aagataattt ctcacaatta gggttttttt tttcttctga gttaactgtt ccatctccat      60
cctaatcttc accttctcct tgatttcgag atctctgtca atttgttgaa tctgttcttt     120
atctaattag ctcaactccg agtctttgct ggattttgaa ggtcaccact gttcaagttt     180 acatttttt  tcctgctaat cgcttgatac ccgtttctgc tgttgtggga tttattgggt     240
ttttcttctt tacgattttt gttgcagctt ttgtagctga agcaaatttg taatctgtga     300
tggtgtatgc actgattctg ggtatggtat tgtactctag gatctcgtag cgagaatgcc     360
aggcattcct cttgttagtc gtgaaacctc ttcgtaagtc tcatgaacaa cctaatgctt     420
ctataatgtc tctgcagcat tgtgtaactt tatactgttt ctcttatgta taagctgagg     480
aatcctagta attcaaactt atcaaatttt tattttgttg tggggttgct tacaattttg     540
gttgcgtatg atggtgaaat cacagttgtt caagaagcac agagcag atg tgc cat       596
                                                    Met Cys His
                                                      1 gaa gac tcc cgt ctg cgt att tcg gaa gag gag gag att gct gct gaa       644
Glu Asp Ser Arg Leu Arg Ile Ser Glu Glu Glu Glu Ile Ala Ala Glu
      5                  10                  15 gag agc ttg gct gcc tat tgc aag cct gtt gaa ctc tac aat atc att       692
```

```
                           -continued

Glu Ser Leu Ala Ala Tyr Cys Lys Pro Val Glu Leu Tyr Asn Ile Ile
 20                  25                  30                  35 caa cgc cgt gct att agg aat gtatgtcttc cttcctacct tttttagaca gaat      747
Gln Arg Arg Ala Ile Arg Asn
                 40 atgtttagtt atgacttatg agctcagctg atatatcaca tgtattggtt tactttttgag    807 ttttgacaat gaaaatttac atgaaaatgt agtttgagtt gacttcattt ggtataagca     867 agtatgtgtt gtcttgctat gcagtccatc ctaatcattt ctctctctct gtctcccctg     927 tag ccc ttg ttt ctt cag cga tgt ttg cat tat aag att gag gca aaa       975
    Pro Leu Phe Leu Gln Arg Cys Leu His Tyr Lys Ile Glu Ala Lys
                 45                  50                  55 cat aaa agg ag gtaagctttt ttttttttcct tcctttctct gttcagaatc tccatt    1032
His Lys Arg Arg
           60 acttttgggt aactattaca ctatacctta gtaattcatt ccggacttga atgctttcta     1092 agttttcgga tagttatcaa tatatattac tgctttgcag a ata caa atg act gta     1148
                                             Ile Gln Met Thr Val
                                                              65 ttc ctc tcg ggc gct ata gat gct ggg gta caa act caa aaa tta ttc       1196
Phe Leu Ser Gly Ala Ile Asp Ala Gly Val Gln Thr Gln Lys Leu Phe
                 70                  75                  80 cct ctg tat att ttg ttg gca aga ctc gtt tct cct aag cct gtc gct       1244
Pro Leu Tyr Ile Leu Leu Ala Arg Leu Val Ser Pro Lys Pro Val Ala
                 85                  90                  95 gag gtatgcattt gaacctcaga cagatttgca ttgatcttta ttatttgtaa cttacc     1303
Glu tattctttgc taacattttt cttgaaattc tcaaattata g tat tct gca gta tat     1359
                                             Tyr Ser Ala Val Tyr
                                                              100 agg ttc agt cga gca tgt atc cta act ggt gga ttg ggg gtt gat gga       1407
Arg Phe Ser Arg Ala Cys Ile Leu Thr Gly Gly Leu Gly Val Asp Gly
105                 110                 115                 120 gtt agt caa gcc caa gcc aac ttt ctt ctc cct gat atg aat aga ctc       1455
Val Ser Gln Ala Gln Ala Asn Phe Leu Leu Pro Asp Met Asn Arg Leu
                125                 130                 135 gca ttg gag gca aaa tca gga tca ctc gct atc ttg ttt atc agc ttt g     1504
Ala Leu Glu Ala Lys Ser Gly Ser Leu Ala Ile Leu Phe Ile Ser Phe
                140                 145                 150 gtgattaaga ctgactgtgt acaaaattat ataaagacat ttatatatgt acagtattca     1564
gataaactga tcacataatt ttcttcttgt ag ct ggt gcg caa aat tct caa        1616
                                   Ala Gly Ala Gln Asn Ser Gln
                                                       155 ttt ggc att gat tca ggc aag att cat tca g gtacttccat ttcttcattg a     1668
Phe Gly Ile Asp Ser Gly Lys Ile His Ser
160                 165 tataacattc taatattgaa aagttatgta tctttgggca ttaccaattt tccatgtaat     1728
agtatggaaa atctcagtcc tatttattaa caaaagaatt agggattctt tgactccaat    1788
tataagagtt tctgaaagtc ttttttttca ttaactctta ccatcggaag cgttttttc     1848 tgccag ga aat ata gga gga cat tgt tta tgg agc aaa ata cct ctg caa    1898
       Gly Asn Ile Gly Gly His Cys Leu Trp Ser Lys Ile Pro Leu Gln
               170                 175                 180 tca ctg tat gcg tcg tgg cag aaa tca cca aac atg gac ttg gga cag       1946
Ser Leu Tyr Ala Ser Trp Gln Lys Ser Pro Asn Met Asp Leu Gly Gln
185                 190                 195                 200 aga gta gac aca gtc tct ctt gtt gaa atg cag cct tgc ttc ata aag g     1995
```

```
Arg Val Asp Thr Val Ser Leu Val Glu Met Gln Pro Cys Phe Ile Lys
            205                 210                 215 taaacactat tgcccaagtc ttcctcttgt tctatgactt tatgctccct gtattgaaat      2055
aaggactgtg tattgaactt cttttgttat ttgaaaaagt aaattggaag taattgctac      2115
tgtgaatttt atttttgcca ttagttttca gtcttgatta tttaaatgaa atattacgg       2175 tataacttgt ccattgctgc ag cta aag tcc atg agt gag gaa aag tgt gtc      2227
                         Leu Lys Ser Met Ser Glu Glu Lys Cys Val
                                     220                 225 tcg att cag gtg ccc agc aat cca ctc acc tcg gtaactttgc acactttgct     2280
Ser Ile Gln Val Pro Ser Asn Pro Leu Thr Ser
        230                 235 atacttccat acattattct gaaatatcat gtaatcatat tcttacaatt cttacacttc     2340
ttatttgaag agc tct ccg cag caa gtg caa gtc acc ata tct gca gaa        2389
             Ser Ser Pro Gln Gln Val Gln Val Thr Ile Ser Ala Glu
                 240                 245                 250 gaa gtt ggg tca acg gaa aaa tct cct tat agt tca ttt tca tat aat       2437
Glu Val Gly Ser Thr Glu Lys Ser Pro Tyr Ser Ser Phe Ser Tyr Asn
                255                 260                 265 gac atc tct tcc tct tcc ttg ttg caa att atc ag gtaatcttca gtttagt     2489
Asp Ile Ser Ser Ser Ser Leu Leu Gln Ile Ile Arg
        270                 275 ctgcaatttc ttctgcgctc tcagatttct tgcctcatct cattatgatt ttttgtaatt     2549
gtataaaata tattggccgg tctgctatct cccttaatat atagttggca gttttcttga     2609
attgtgactg tcctcctctt ttatggggat tatacaagtc gttacgtaca actaaaaatg     2669
tccatctcgt taagttgact ctataccact acattcattg catag g ttg aga aca       2724
                                                   Leu Arg Thr
                                                           280 gga aat gta gtt ttc aac tac aga tac tat aac aac aaa ttg cag aag       2772
Gly Asn Val Val Phe Asn Tyr Arg Tyr Tyr Asn Asn Lys Leu Gln Lys
            285                 290                 295 act gaa g gtaactagta ttattttaac ctgtttcata cccatgtgtg tctatatttc      2829
Thr Glu
atccgttacc ctaacctgtt acgtatatgt ttgctatgtg tcttgcag ta act gaa       2885
                                                      Val Thr Glu
                                                              300 gac ttt tct tgt cca ttc tgc tta gta aaa tgt gcc agt ttc aag gtgga     2935
Asp Phe Ser Cys Pro Phe Cys Leu Val Lys Cys Ala Ser Phe Lys
        305                 310                 315 ctttcatttc cattctcatt catcctctta gtcaaagata cagctgtagt gactagtctt     2995
tgtagtgatg caatcttttc tttttctccc aatcatgttg tag ggc ctg aga tat      3050
                                                Gly Leu Arg Tyr
                                                            320 cac ttg cca tca acc cac gat ctc ctc aat ttc gag ttt tgg gttgtagct     3101
His Leu Pro Ser Thr His Asp Leu Leu Asn Phe Glu Phe Trp
        325                 330                 335 ttaaaattca gttaacctgt ttgatctttt ttttttattt tgtgggtgcc actaatctgc     3161
tttacttggt tag gta act gaa gaa ttt cag gcg gta aat gtc tcc ctc       3210
                Val Thr Glu Glu Phe Gln Ala Val Asn Val Ser Leu
                                340                 345 aag act gag aca atg ata tcc aag gttagaacat cttgtttgtt cgatttatgt     3264
Lys Thr Glu Thr Met Ile Ser Lys
        350                 355 tcattagttt ctctgctgta tatcttatag gctgtaacaa attcatttttt catttaaact    3324 aatatcctcc atgggttgtt gacttttgtg tggttaaata agggaactgg aatctttagt    3384
```

```
tgctatttgt cacactatga tccttgctat tgtccttaat agcgtgatga gaataaactc      3444
aaaatgacat cgctgttctg tttacttttt gtggccatga gaccgtcaaa gctcgactgt      3504
agaataaagt cctggattat ataggagtgt caaatctaat tgaagtagtt ggttctacaa      3564
tatattctat gtctttgtag ttttttcctat ttgatgatta ctcttagcac agttttctaa    3624
atgttaatgt tcattaaaaa atctgctcag gtt aat gag gat gac gtt gac cca      3678
                                  Val Asn Glu Asp Asp Val Asp Pro
                                                          360 aag cag caa act ttc ttt ttt tc gtaagttatc tggcctatat gttgcctttt       3731
Lys Gln Gln Thr Phe Phe Phe Ser
    365                 370 attatctttc cagcatctgt gtgagaccat aaaaattctt caatatgtga cag t tcc      3788
                                                               Ser aaa aaa ttc aga cgg agg agg caa aag agt cag gta cgg agc tca agg       3836
Lys Lys Phe Arg Arg Arg Arg Gln Lys Ser Gln Val Arg Ser Ser Arg
        375                 380                 385 caa ggg cct cat ctt gga tta ggt tgc gag gtg cta gat aag act gat g     3885
Gln Gly Pro His Leu Gly Leu Gly Cys Glu Val Leu Asp Lys Thr Asp
        390                 395                 400 gtatgtgttt gactgaaatg acagttaatt ggatttgtag tattggcttc ttttgtgatg     3945
agagcctgtc ttagttgtat attttacgag tattttactt tgttatgtgc aattttgcat     4005
gcaacaacgt tggatcattt ggcacagctt tttattctta ctttcag at gct cat        4060
                                                      Asp Ala His
                                                              405 tct gtt aga agt gag aag agc cga ata cca cct gga aag cat tac gaa       4108
Ser Val Arg Ser Glu Lys Ser Arg Ile Pro Pro Gly Lys His Tyr Glu
        410                 415                 420 aga att ggg ggt gct gag tct ggt caa aga gtt cct cct ggc acg agt       4156
Arg Ile Gly Gly Ala Glu Ser Gly Gln Arg Val Pro Pro Gly Thr Ser
        425                 430                 435 cct gca gac gtg caa tca tgt ggg gat cca gat tat gtg cag tcg ata       4204
Pro Ala Asp Val Gln Ser Cys Gly Asp Pro Asp Tyr Val Gln Ser Ile
440                 445                 450                 455 gct gga agt aca atg ttg cag ttt gca aaa acg agg aaa ata tct ata       4252
Ala Gly Ser Thr Met Leu Gln Phe Ala Lys Thr Arg Lys Ile Ser Ile
                460                 465                 470 gaa cgg tcg gac ttg agg aa gtatgtttga cttccttttg tcgttctatc ctctt     4307
Glu Arg Ser Asp Leu Arg Asn
                475 cttcaattta tatttaacta catatggttc atgcatgaaa aattgtgtcc tagttttata     4367 acaagtagct tgttaatccc aaatgatgtg agtgagtttt tcaaattttt tcctcctcca     4427 g c cga agc ctc ctt cag aag aga cag ttc ttc cac tct cat cga gct       4474
  Arg Ser Leu Leu Gln Lys Arg Gln Phe Phe His Ser His Arg Ala
      480                 485                 490 cag gtgatctttt ttctttagct ctcttgcttt tgaagattgc aattgatttt gactttt    4533
Gln gctatgtgta ctatcgcag ccc atg gct cta gaa caa gta ctt tcg gac cgg      4585
                       Pro Met Ala Leu Glu Gln Val Leu Ser Asp Arg
                                495                 500         505 gat agt gaa gat gaa gtt gat gat gat gtg gca gat ttt gaa gat aga       4633
Asp Ser Glu Asp Glu Val Asp Asp Asp Val Ala Asp Phe Glu Asp Arg
                510                 515                 520 agg gtatgttttt gaatttaata ttttcaccgc atcagtagtt gggtagaata aagctc     4692
Arg agtagttggg tagatatatg tttcatgtga aagggaaagg aatattgaag actgggcatg     4752
```

```
ggcaaacgtt aggagcaata ttgtaatggt tcagagatca atagaaaata tgtgagcaag    4812
cctcacggtt tgatatggaa cagtagaacc agatcattag tgcttatata acactcatta    4872
aaagacgaag tgtgtccgtt tgtactcgat tctaacatag ttgattctaa catagtttgt    4932
ctgattctcc atatagtgaa taacgttatt tcctattact attctttcag atg ctc       4988
                                                       Met Leu gat gat ttc gtt gat gtg act aaa gat gag aaa cag atg atg cac atg      5036
Asp Asp Phe Val Asp Val Thr Lys Asp Glu Lys Gln Met Met His Met
525                 530                 535                 540 tgg aac tcg ttt gtg agg aag cag cg gtatgtctta tctcttttca gtacatgt    5090
Trp Asn Ser Phe Val Arg Lys Gln Arg
                545 cacgtggagt tttccagtat aaacatttag agtcgcgcat gtaaaggttg tggataattc    5150 ctgcctgggt tcttctggtt aaaaaaaaaa aactgaacaa ttagataaca tacgcatcca    5210 tgttctctga ctcattataa gcattacctt gacagtggtt ttggacccct tgcag a       5266 gta tta gca gat ggt cac att cca tgg gca tgc gag gca ttc tca aga      5314
Val Leu Ala Asp Gly His Ile Pro Trp Ala Cys Glu Ala Phe Ser Arg
550                 555                 560                 565 ttg cac gga ccc atc atg gtt cga aca ccg cac ttg att tg gtaattcaac    5365
Leu His Gly Pro Ile Met Val Arg Thr Pro His Leu Ile Trp
                570                 575 tctcatttct tccattgttt tttccagtgt atcggagaag aaagcggttt tgttgataaa    5425
agtgagcttt ttttgtgtag g tgc tgg aga gtg ttt atg gtg aaa ctg tgg      5476
                       Cys Trp Arg Val Phe Met Val Lys Leu Trp
                       580                 585 aac cac ggt ctt ctt gat gcc cga acc atg aac aac tgt aat acc ttt      5524
Asn His Gly Leu Leu Asp Ala Arg Thr Met Asn Asn Cys Asn Thr Phe
590                 595                 600                 605 ctc gaa cag ctc caa att tgaaaaccca agaaatcatt aatttaagta gaaaaaca    5580
Leu Glu Gln Leu Gln Ile
                610

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 4
ggatccgaac ccgactcggt acc                                              23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 5
gcttatggat gtggactctc taac                                             24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence
```

-continued

<400> SEQUENCE: 6
aggtcctaca actacaacag tt         22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 7
gaggaagcta gtattctctt tg         22

<210> SEQ ID NO 8
<211> LENGTH: 604
<212> TYPE: PRT
<213> ORGANISM: Oryza sativa
<220> FEATURE:
<221> NAME/KEY: ZN_FING
<222> LOCATION: (310)..(335)

<400> SEQUENCE: 8

```
Met Cys Arg His Gln Pro Arg Ala Arg Leu Ser Pro Asp Glu Gln Leu
  1               5                  10                  15

Ala Ala Glu Glu Ser Phe Ala Leu Tyr Cys Lys Pro Val Glu Leu Tyr
             20                  25                  30

Asn Ile Ile Gln Arg Arg Ser Ile Lys Asn Pro Ala Phe Leu Gln Arg
         35                  40                  45

Cys Leu Leu Tyr Lys Ile His Ala Arg Arg Lys Lys Arg Ser Leu Ile
     50                  55                  60

Thr Ile Ser Leu Ser Gly Gly Thr Asn Lys Glu Leu Arg Ala Gln Asn
 65                  70                  75                  80

Ile Phe Pro Leu Tyr Val Leu Leu Ala Arg Pro Thr Asn Asn Val Ser
                 85                  90                  95

Leu Glu Gly His Ser Pro Ile Tyr Arg Phe Ser Arg Ala Cys Leu Leu
            100                 105                 110

Thr Ser Phe His Glu Phe Gly Asn Lys Asp Tyr Thr Glu Ala Thr Phe
        115                 120                 125

Val Ile Pro Asp Val Lys Asn Leu Ala Thr Ser Arg Ala Cys Ser Leu
    130                 135                 140

Asn Ile Ile Leu Ile Ser Cys Gly Arg Ala Glu Gln Thr Phe Asp Asp
145                 150                 155                 160

Asn Asn Cys Ser Gly Asn His Val Glu Gly Ser Thr Leu Gln Lys Leu
                165                 170                 175

Glu Gly Lys Cys Phe Trp Gly Lys Ile Pro Ile Asp Leu Leu Ala Ser
            180                 185                 190

Ser Leu Gly Asn Cys Val Ser Leu Ser Leu Gly His Thr Val Glu Met
        195                 200                 205

Ser Ser Thr Val Glu Met Thr Pro Ser Phe Leu Glu Pro Lys Phe Leu
    210                 215                 220

Glu Asp Asp Ser Cys Leu Thr Phe Cys Ser Gln Lys Val Asp Ala Thr
225                 230                 235                 240

Gly Ser Phe Gln Leu Gln Val Ser Ile Ser Ala Gln Glu Ala Gly Ala
                245                 250                 255

Lys Asp Met Ser Glu Ser Pro Tyr Ser Val Tyr Ser Tyr Asn Asp Val
            260                 265                 270
```

```
Pro Pro Ser Ser Leu Thr His Ile Ile Arg Leu Arg Ser Gly Asn Val
            275                 280                 285

Leu Phe Asn Tyr Lys Tyr Tyr Asn Asn Thr Met Gln Lys Thr Glu Val
        290                 295                 300

Thr Glu Asp Phe Ser Cys Pro Phe Cys Leu Val Pro Cys Gly Ser Phe
305                 310                 315                 320

Lys Gly Leu Gly Cys His Leu Asn Ala Ser His Asp Leu Phe His Tyr
                325                 330                 335

Glu Phe Trp Ile Ser Glu Glu Cys Gln Ala Val Asn Val Ser Leu Lys
            340                 345                 350

Thr Asp Ser Trp Arg Thr Glu Leu Leu Ala Glu Gly Val Asp Pro Arg
        355                 360                 365

His Gln Thr Phe Ser Tyr Arg Ser Arg Phe Lys Lys Arg Lys Arg Val
    370                 375                 380

Glu Ile Ser Ser Asp Lys Ile Arg His Val His Pro His Ile Val Asp
385                 390                 395                 400

Ser Gly Ser Pro Glu Asp Ala Gln Ala Gly Ser Glu Asp Asp Tyr Val
                405                 410                 415

Gln Arg Glu Asn Gly Ser Ser Val Ala His Ala Ser Val Asp Pro Ala
            420                 425                 430

Asn Ser Leu His Gly Ser Asn Leu Ser Ala Pro Thr Val Leu Gln Phe
        435                 440                 445

Gly Lys Thr Arg Lys Leu Ser Val Glu Arg Ala Asp Pro Arg Asn Arg
    450                 455                 460

Gln Leu Leu Gln Lys Arg Gln Phe Phe His Ser His Arg Ala Gln Pro
465                 470                 475                 480

Met Ala Trp Ser Lys Val Phe Ser Asp Arg Asp Ser Glu Asp Glu Val
                485                 490                 495

Asp Asp Asp Ile Ala Asp Phe Glu Asp Arg Arg Met Leu Asp Asp Phe
            500                 505                 510

Val Asp Val Thr Lys Asp Glu Lys Leu Ile Met His Met Trp Asn Ser
        515                 520                 525

Phe Val Arg Lys Gln Arg Val Leu Ala Asp Gly His Ile Pro Trp Ala
    530                 535                 540

Cys Glu Ala Phe Ser Gln Phe His Gly Gln Glu Leu Val Gln Asn Pro
545                 550                 555                 560

Ala Leu Leu Trp Cys Trp Arg Phe Phe Met Val Lys Leu Trp Asn His
                565                 570                 575

Ser Leu Leu Asp Ala Arg Ala Met Asn Ala Cys Asn Thr Ile Leu Glu
            580                 585                 590

Gly Tyr Leu Asn Gly Ser Ser Asp Pro Lys Lys Asn
        595                 600

<210> SEQ ID NO 9
<211> LENGTH: 2248
<212> TYPE: DNA
<213> ORGANISM: Oryza sativa
<220> FEATURE:
<221> NAME/KEY: CDS
<222> LOCATION: (86)..(1897)
<221> NAME/KEY: misc_feature
<222> LOCATION: (36)..(41)
<223> OTHER INFORMATION: NheI recognition site

<400> SEQUENCE: 9
cgccgatccc catccctccc gcgagcagga gcagggctag ccgtcgttcc tcctgctgct      60
```

```
tccgccgcat ccatcctgat accag atg tgc cgc cac cag cca agg gct cgg        112
                            Met Cys Arg His Gln Pro Arg Ala Arg
                             1               5 ctc tct ccc gat gag cag ctt gca gct gaa gaa agc ttc gca tta tac        160
Leu Ser Pro Asp Glu Gln Leu Ala Ala Glu Glu Ser Phe Ala Leu Tyr
 10              15                  20                  25 tgc aag ccg gtc gag ttg tat aat atc att cag cgc cga tcc att aaa        208
Cys Lys Pro Val Glu Leu Tyr Asn Ile Ile Gln Arg Arg Ser Ile Lys
             30                  35                  40 aat cct gct ttt ctt caa aga tgc ctt ctt tac aag att cac gca aga        256
Asn Pro Ala Phe Leu Gln Arg Cys Leu Leu Tyr Lys Ile His Ala Arg
         45                  50                  55 cgg aag aag agg agc ctg ata acc ata tca ctt tct gga ggc aca aat        304
Arg Lys Lys Arg Ser Leu Ile Thr Ile Ser Leu Ser Gly Gly Thr Asn
     60                  65                  70 aaa gaa ctg cgg gca caa aat atc ttt cct ctt tat gtt ctg tta gct        352
Lys Glu Leu Arg Ala Gln Asn Ile Phe Pro Leu Tyr Val Leu Leu Ala
 75                  80                  85 aga cct act aat aat gtt tca ctt gaa ggg cat tct ccg ata tat cga        400
Arg Pro Thr Asn Asn Val Ser Leu Glu Gly His Ser Pro Ile Tyr Arg
 90                  95                 100                 105 ttc agt cgt gct tgt ttg ttg act tct ttt cat gaa ttt gga aat aaa        448
Phe Ser Arg Ala Cys Leu Leu Thr Ser Phe His Glu Phe Gly Asn Lys
                110                 115                 120 gac tac act gaa gca aca ttc gtc att cct gat gtg aag aac tta gca        496
Asp Tyr Thr Glu Ala Thr Phe Val Ile Pro Asp Val Lys Asn Leu Ala
            125                 130                 135 acc tcc cga gct tgc agc ctt aat att atc ctt atc agc tgt gga cga        544
Thr Ser Arg Ala Cys Ser Leu Asn Ile Ile Leu Ile Ser Cys Gly Arg
            140                 145                 150 gct gag caa act ttt gat gac aat aac tgt tct ggg aac cat gtg gaa        592
Ala Glu Gln Thr Phe Asp Asp Asn Asn Cys Ser Gly Asn His Val Glu
        155                 160                 165 ggc tct act ctc caa aag ctt gaa ggg aag tgt ttc tgg ggt aaa ata        640
Gly Ser Thr Leu Gln Lys Leu Glu Gly Lys Cys Phe Trp Gly Lys Ile
170                 175                 180                 185 cca atc gat ctt ctt gct tca tct ttg gga aat tgt gtg agc tta agt        688
Pro Ile Asp Leu Leu Ala Ser Ser Leu Gly Asn Cys Val Ser Leu Ser
                190                 195                 200 ttg gga cat acc gtg gaa atg tct tcc acg gtt gag atg acc cca agc        736
Leu Gly His Thr Val Glu Met Ser Ser Thr Val Glu Met Thr Pro Ser
            205                 210                 215 ttc tta gag cca aaa ttt ctg gag gat gac agt tgc ttg aca ttt tgc        784
Phe Leu Glu Pro Lys Phe Leu Glu Asp Asp Ser Cys Leu Thr Phe Cys
        220                 225                 230 tct cag aag gtt gat gct act ggt tca ttt caa ctg caa gtt agc ata        832
Ser Gln Lys Val Asp Ala Thr Gly Ser Phe Gln Leu Gln Val Ser Ile
    235                 240                 245 tct gct caa gag gct ggt gca aaa gac atg tcc gag tct cct tat agt        880
Ser Ala Gln Glu Ala Gly Ala Lys Asp Met Ser Glu Ser Pro Tyr Ser
250                 255                 260                 265 gtt tat tca tat aat gat gtg cca cct tcg tca ttg aca cat att ata        928
Val Tyr Ser Tyr Asn Asp Val Pro Pro Ser Ser Leu Thr His Ile Ile
                270                 275                 280 agg ttg aga tct ggc aat gtg ctt ttt aac tac aaa tac tac aat aat        976
Arg Leu Arg Ser Gly Asn Val Leu Phe Asn Tyr Lys Tyr Tyr Asn Asn
            285                 290                 295 act atg caa aaa acc gaa gtc act gaa gat ttt tct tgc cca ttt tgc       1024
Thr Met Gln Lys Thr Glu Val Thr Glu Asp Phe Ser Cys Pro Phe Cys
```

-continued

```
              300                 305                     310
ttg gta cca tgt ggc agc ttt aag ggt cta gga tgt cac cta aac gca    1072
Leu Val Pro Cys Gly Ser Phe Lys Gly Leu Gly Cys His Leu Asn Ala
315                 320                     325 tcg cat gac ctt ttc cat tat gag ttt tgg ata tct gaa gag tgc cag    1120
Ser His Asp Leu Phe His Tyr Glu Phe Trp Ile Ser Glu Glu Cys Gln
330                 335                     340                 345 gct gtt aat gtt agt ctg aag act gat tct tgg aga aca gag ctt ttg    1168
Ala Val Asn Val Ser Leu Lys Thr Asp Ser Trp Arg Thr Glu Leu Leu
                350                 355                     360 gct gag gga gtt gat cca aga cat caa aca ttt tcg tac cgc tca aga    1216
Ala Glu Gly Val Asp Pro Arg His Gln Thr Phe Ser Tyr Arg Ser Arg
                365                 370                     375 ttt aag aag cgt aaa agg gtg gaa atc tca agt gat aaa att agg cat    1264
Phe Lys Lys Arg Lys Arg Val Glu Ile Ser Ser Asp Lys Ile Arg His
            380                 385                     390 gta cat cca cat att gtg gat tca gga tca cct gaa gat gcc cag gca    1312
Val His Pro His Ile Val Asp Ser Gly Ser Pro Glu Asp Ala Gln Ala
395                 400                     405 gga tct gaa gac gat tac gtg cag agg gaa aat ggt agt tct gta gca    1360
Gly Ser Glu Asp Asp Tyr Val Gln Arg Glu Asn Gly Ser Ser Val Ala
410                 415                     420                 425 cac gct tct gtt gat cct gct aat tca tta cac ggt agc aat ctt tca    1408
His Ala Ser Val Asp Pro Ala Asn Ser Leu His Gly Ser Asn Leu Ser
                430                 435                     440 gca cca aca gtg tta cag ttt ggg aag aca aga aag ctg tct gtt gaa    1456
Ala Pro Thr Val Leu Gln Phe Gly Lys Thr Arg Lys Leu Ser Val Glu
                445                 450                     455 cga gct gat ccc aga aat cgg cag ctc cta caa aaa cgc cag ttc ttt    1504
Arg Ala Asp Pro Arg Asn Arg Gln Leu Leu Gln Lys Arg Gln Phe Phe
            460                 465                     470 cat tct cac agg gct caa cca atg gca tgg agc aaa gtt ttc tca gat    1552
His Ser His Arg Ala Gln Pro Met Ala Trp Ser Lys Val Phe Ser Asp
475                 480                     485 cgt gat agt gaa gat gaa gtt gat gat gac att gct gat ttt gaa gat    1600
Arg Asp Ser Glu Asp Glu Val Asp Asp Asp Ile Ala Asp Phe Glu Asp
490                 495                     500                 505 aga aga atg ctt gat gat ttt gtt gat gtt aca aaa gac gag aaa ctt    1648
Arg Arg Met Leu Asp Asp Phe Val Asp Val Thr Lys Asp Glu Lys Leu
                510                 515                     520 att atg cat atg tgg aat tca ttt gtt cgg aaa caa agg gta cta gcg    1696
Ile Met His Met Trp Asn Ser Phe Val Arg Lys Gln Arg Val Leu Ala
                525                 530                     535 gat ggc cat att ccc tgg gca tgc gaa gca ttc tcg cag ttt cat gga    1744
Asp Gly His Ile Pro Trp Ala Cys Glu Ala Phe Ser Gln Phe His Gly
                540                 545                     550 caa gaa ctt gta caa aat cca gct cta cta tgg tgt tgg agg ttt ttt    1792
Gln Glu Leu Val Gln Asn Pro Ala Leu Leu Trp Cys Trp Arg Phe Phe
            555                 560                     565 atg gtc aaa ctc tgg aac cac agt cta ctg gat gcg cga gcc atg aat    1840
Met Val Lys Leu Trp Asn His Ser Leu Leu Asp Ala Arg Ala Met Asn
570                 575                     580                 585 gcc tgc aac aca att ctt gaa ggc tac ctg aac gga agc tcg gat cca    1888
Ala Cys Asn Thr Ile Leu Glu Gly Tyr Leu Asn Gly Ser Ser Asp Pro
                590                 595                     600 aag aaa aat tgacgcatac aaatcattgg ccaacctgta gagtaaaatg            1937
Lys Lys Asn cacttgtact ggttctggcc attccaatag tttgttttgt ttttggaaaa aaagatgtct  1997
```

```
gaagaattga aagctaacat gtgttttgga gggaagaaaa ttgaaggctg gggcggtcat    2057
tgtttcattt agaactcttc tcgattctat ttattgtaat tgatgttact cataactgta    2117
gagcagtatc aagaccaaac tgtaatgata tggttagcaa tatttacata aaagtttatt    2177
ttgtttgttg tttagcaccg tgggcagaca atttaattcc tatgcaggcc cttttcatc    2237 gtcaaaaaaa a                                                          2248

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 10
gacgagaaac ttattatgca tatg                                            24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 11
ggtcttgata ctgctctaca gttatg                                          26

<210> SEQ ID NO 12
<211> LENGTH: 7
<212> TYPE: PRT
<213> ORGANISM: Arabidopsis thaliana

<400> SEQUENCE: 12

Lys Arg Gln Phe Phe His Ser
  1               5

<210> SEQ ID NO 13
<211> LENGTH: 6
<212> TYPE: PRT
<213> ORGANISM: Arabidopsis thaliana

<400> SEQUENCE: 13

Trp Ala Cys Glu Ala Phe
  1               5

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 14
aagcggcaat tttaycaytc                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence
```

```
<400> SEQUENCE: 15
aagcggcagt tctaycaytc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 16
aagcggcagt tctaycayag                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence

<400> SEQUENCE: 17
aagcggcaat tttaycayag                                              20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence
<221> NAME/KEY: misc-feature
<222> LOCATION: 12
<223> OTHER INFORMATION: n is a or t or c or g

<400> SEQUENCE: 18
aatacctcac angccca                                                 17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Oligonucleotide Primer Sequence
<221> NAME/KEY: misc-feature
<222> LOCATION: 12
<223> OTHER INFORMATION: n is a or t or c or g

<400> SEQUENCE: 19
aatacttcgc angccca                                                 17

<210> SEQ ID NO 20
<211> LENGTH: 1216
<212> TYPE: DNA
<213> ORGANISM: Beta vulgaris
<220> FEATURE:
<221> NAME/KEY: misc_feature
<222> LOCATION: (1)..(20)
<223> OTHER INFORMATION: Oligonucleotide Primer "KR1" Sequence
<221> NAME/KEY: CDS
<222> LOCATION: (21)..(33)
<221> NAME/KEY: intron
<222> LOCATION: (34)..(694)
<221> NAME/KEY: CDS
<222> LOCATION: (695)..(778)
<221> NAME/KEY: intron
```

-continued

```
<222> LOCATION: (779)..(951)
<221> NAME/KEY: CDS
<222> LOCATION: (952)..(1031)
<221> NAME/KEY: intron
<222> LOCATION: (1032)..(1174)
<221> NAME/KEY: CDS
<222> LOCATION: (1175)..(1199)
<221> NAME/KEY: misc_feature
<222> LOCATION: (1200)..(1216)
<223> OTHER INFORMATION: Oligonucleotide Primer "WA2" Sequence

<400> SEQUENCE: 20
aagcggcaat tttatcattc t cac aga gct cag gtaatcaact gcagaagtca tat        56
                         His Arg Ala Gln cgtgttatgc tgatgtctga actcctataa tataacagtt gttgactctt tgtttcctat       116
agtagttgtc ttgatggttg atcaaatttt gacaacattt cagcattctt aaacatcttt       176
tcattatttt ttatttacaa agagtagtaa ttcaagcacc ataagaaaca ctgatcaata       236
gtttcttgca agttcttgaa cacttaataa gcagaggggt acttttaaat attcagcatt       296
tgtttgataa tctcaggtgt tttggacttg ctatatgtac ctgatgacac cgctttagtt       356
tcaactagga tatggcgcta aatgggggaa aattgataaa gtcgagtagc aaaaatgatt       416
aggattttaa cgtggtgttt ctcctttttct ctctcaagtt cattgtggtg tgccatctat      476
agaaatgtct cgggttgtac ttttttctatg gaaatgcagg cgtcgtttca gagtttgttc      536
tctgcttctc tcaatagtca attcagataa gccactttca ctgcaacctt gactgctact       596
cttggacttc aaattctagt cctctttgtc tttgtatcat tcttcaattt ttccaattga       656
tgatgctgat tttgaaaaac tcctctttgc acccgaag cca atg gct ctg gat caa       712
                                            Pro Met Ala Leu Asp Gln
                                                   5              10 gta ttg tca gac agg gat agt gag gat gaa gtg gat gat gat att gct        760
Val Leu Ser Asp Arg Asp Ser Glu Asp Glu Val Asp Asp Asp Ile Ala
             15                  20                  25 gct ctt gaa gat aga agg gtacgtttgg ttattttcca aattttttga gttgcttg      816
Ala Leu Glu Asp Arg Arg
           30 cgtgattaac aattttttgat ctagtaatgg ttcttgcttc tagccaagtc tttgaatttc      876 taatgtaata gttatctttt tcttgagtgc attttgctaa ctaaaccgtg tatggtacct      936 tgccttgtgc tgcag atg ctt gat gat ttt gtg gat gta agc aaa gac gaa       987
              Met Leu Asp Asp Phe Val Asp Val Ser Lys Asp Glu
                 35                  40 aaa cac cta atg cat cta tgg aac tca ttt gta aaa aag caa ag gtagac     1037
Lys His Leu Met His Leu Trp Asn Ser Phe Val Lys Lys Gln Arg
 45                  50                  55 tttgttatgc aattgtcccg tttgtttaat ttctttctcc attgtgaatg cttgcgtagt     1097
gtgctcccga agtattttttg atggcgctta cctgtggttg tttggctttg tgtaatgttt     1157
ccatttttgt gcaccag g gtt ttg gct gat ggt cat gtt ccc tgggcatgcg a     1210
                   Val Leu Ala Asp Gly His Val Pro
                                  60                  65 agtatt                                                                1216
```

ARABIDOPSIS MPC1 GENE AND METHODS FOR CONTROLLING FLOWERING TIME

FIELD OF THE INVENTION

The present invention relates to genes for floral regulation of plants and to methods for controlling plant flowering by regulating the expression of said gene. The present invention also relates to transgenic plants whose flowering time is modified in comparison with wild type plants by regulating the expression of said gene and to methods for generating said transgenic plants.

BACKGROUND OF THE INVENTION

In order to resolve the worldwide food problem, developing technology for increasing the yield of food using biotechnology has been desired. Grain, which is one of main crops, is seed of plants and some vegetables are fruit of plants. For productivity increase of these plants, floral regulation for controlling growth of plants is an important key technology. On the other hand, flowering inhibition of vegetables, whose vegetative organs such as leaves or roots are marketed, prevents vegetative organs from stopping their growth and often increases their productivity. In addition, for many crops the suitable cultivating places are limited because of their species specificity of hereditary flowering behavior depending on environment. Modification of these properties by flowering regulation can expand the suitable cultivating places.

In molecular genetic studies using model plants such as *Arabidopsis thaliana* and *Antirrhinum majas,* many genes involved in identity determination of floral meristems or morphogenesis of floral organs have been isolated. Among these genes LEAFY and APETALA-1 genes are known to be forcedly expressed in the host plant Arabidopsis or poplar when introduced into these plants, thereby flowering the plants earlier. Since these genes are not fundamentally involved in floral budding (the transition from vegetative growth to reproductive growth), the use of these genes alone cannot arbitrarily regulate flowering. If the function of these genes is inhibited, the shape of inflorescence is changed, which is obvious from the phenotype of the mutants, and flowering cannot be regulated.

The embryonic flower mutant of Arabidopsis, in which flowering occurs immediately after germination, is known (Sung et al. (1992), Science, vol.258: p1645–). In this mutant, the function of a gene that maintains vegetative growth for a certain period of time after germination is thought to be lost. The flowering of wild-type Arabidopsis is thought to be inhibited by the expression of this gene. Although the approximate location of this gene on the chromosome is reported (Yang et al. (1995), Dev. Biol., vol.169: p421–), the result is far from helping the isolation of the gene and the gene has not yet been isolated.

SUMMARY OF THE INVENTION

An objective of the present invention is to isolate a gene for floral regulation (flowering regulating gene) and to provide a transgenic plant into which the gene is introduced. If a fundamental gene that regulates flowering is isolated, flowering time can be freely controlled by artificially regulating this gene.

The present inventors have succeeded in isolating mutant Arabidopsis that exhibits flowering immediately after germination because the function of the flowering regulating gene is lost and in identifying a single gene, which was mutated, in a wide region of the chromosome and isolating it. Furthermore, the present inventors have confirmed that this gene has flowering inhibiting function by introducing the gene into Arabidopsis and expressing it. Based on these findings, the present inventors have completed the present invention.

Moreover, the present inventors have discovered that the flowering regulating gene isolated from any kind of plant by hybridization or PCR technique based on the sequence of Arabidopsis flowering regulating gene has the function that complements the mutation of the Arabidopsis super early flowering mutant, inhibits flowering, and induces normal differentiation of stems and leaves.

Thus, the present invention relates to novel flowering regulating genes that exist extensively in plants, proteins with flowering regulating activity encoded by said genes, transgenic plants in which the expression of said gene is modified, methods for generating these plants, and methods for controlling the flowering time of plants by regulating the expression of said genes. More specifically, the present invention relates to (1) a DNA encoding a protein having flowering regulating activity, wherein said DNA selected from the group consisting of:
 i) a DNA encoding a protein comprising the amino acid sequence of SEQ ID NO: 1;
 ii) a DNA encoding a protein comprising the amino acid sequence substantially identical to that of SEQ ID NO: 1;
 iii) a DNA hybridizing a DNA encoding the protein comprising the amino acid sequence of SEQ ID NO:1;
 iv) a DNA encoding a protein comprising amino acid sequences showing 50% or more and 60% or more homology with amino acids 278 to 348 and 465 to 607, respectively, of the amino acid sequence of SEQ ID NO: 1;
 v) a DNA encoding a protein comprising the amino acid sequence of SEQ ID NO: 8.
 vi) a DNA encoding a protein comprising the amino acid sequence substantially identical to that of SEQ ID NO: 8.
 vii) a DNA hybridizing a DNA encoding the protein comprising the amino acid sequence of SEQ ID NO: 8; and
 viii) a DNA encoding a protein comprising amino acid sequences showing 50% or more and 60% or more homology with amino acids 282 to 352 and 450 to 592, respectively, of the amino acid sequence of SEQ ID NO: 8.a DNA encoding a protein having flowering regulating activity, wherein said protein comprises the amino acid sequence of SEQ ID NO: 1;

(2) the DNA of (1), wherein said DNA of i) comprises the coding region of the nucleotide sequence of SEQ ID NO: 2;

(3) the DNA of (1), wherein said DNA of v) comprises the coding region of the nucleotide sequence of SEQ ID NO: 9;

(4) the DNA of (1), encoding a protein having a zinc finger structure;

(5) a protein having flowering regulating activity, encoded by the DNA of (1);

(6) the protein of (5), comprising the amino acid sequence of SEQ ID NO: 1 or 8;

(7) a recombinant double-stranded DNA molecule comprising an expression cassette comprising the DNA of (1);

(8) a recombinant double-stranded DNA molecule comprising an expression cassette comprising the following constituent elements of i) to iii),
   i) a promoter that can transcribe in plant cells,
   ii) the DNA of (1) or a part of it fused to said promoter in sense or antisense direction, and selectively, and
   iii) a signal involved in transcription termination of RNA molecules and polyadenylation, wherein the signal functions in plants;
(9) a transformant into which the recombinant double-stranded DNA molecule of (7) is introduced;
(10) a transgenic plant cell into which the recombinant double-stranded DNA molecule of (8) is introduced;
(11) a method for producing a protein of (5), wherein the method comprises
   (a) cultivating a transformant of (9) and
   (b) recovering a recombinant protein from said transformant or the culture supernatant of it;
(12) a transgenic plant comprising transgenic plant cells of (10);
(13) a method for producing a transgenic plant of (12), wherein said method comprises
   (a) introducing the recombinant double-stranded DNA molecule of (8) into plant cells and
   (b) regenerating said plant cells;
(14) a DNA encoding an antisense RNA complementary to a transcription product of a DNA of (1);
(15) a method for regulating the flowering time of a plant, wherein said method comprises introducing the whole or a part of a DNA of (1) or the whole or a part of a DNA of (14) into a plant and expressing it, thereby changing the activity of a flowering regulating protein; and
(16) an antibody that binds to a protein of (5).

BRIEF DESCRIPTION OF THE DRAWINGS

The drawing shows the location of the DNA clones of the chromosome region containing Arabidopsis "MPC1" gene and the markers 16EB53 and z11-1. In the drawing the unfilled arrow shows the position and direction of "MPC1" gene and 11K22, 22K2, 19A20, and 20I12 show DNA clones.

DETAILED DESCRIPTION OF THE INVENTION

"An expression cassette" used herein means a DNA molecule comprising a gene and constituent elements essential for the expression of the gene. Typically, it is a DNA molecule comprising (i) a promoter to express a structural gene in a host, (ii) the structural gene, and, if necessary, (iii) a terminator. The promoter varies depending on the host. For example, in order to produce a recombinant protein in a microorganism, a promoter functioning in the microorganism is used. For generating a transgenic plant, a promoter functioning in plant cells is used. An example of "a recombinant double-stranded DNA molecule comprising an expression cassette" is typically a vector comprising an expression cassette.

The present invention provides novel proteins regulating the flowering of plants and DNAs encoding said proteins. The nucleotide sequences of the cDNA and the genomic DNA of Arabidopsis-derived "MPC1", which has been isolated by the present inventors, are shown in SEQ ID NO: 2 and 3, respectively. The amino acid sequence of Arabidopsis-derived "MPC1" protein encoded by the cDNA or genomic DNA is shown in SEQ ID NO: 1. The nucleotide sequences of the cDNA and the genomic DNA of rice-derived "Os-MPC1", which has been isolated by the present inventors, are shown in SEQ ID NO: 9 and 10, respectively. The amino acid sequence of rice-derived "Os-MPC1" protein encoded by the cDNA or genomic DNA is shown in SEQ ID NO: 8.

The mutation of Arabidopsis-derived "MPC1" gene eliminates normal flowering regulating ability of plants and leads plant to flowering immediately after germination (super early flowering mutation). The present inventors have found that guanine is substituted with adenine at the nucleotide 5039 of "MPC1" genomic DNA (SEQ ID NO: 3) in "mpc1" mutant plants (Example 1). Since the C-terminal amino acid residues from 541 of "MPC1" protein are not translated by this base substitution, the deletion of the amino acid sequence after this mutation point is thought to diminish the normal flowering regulating function of "MPC1" protein. In other words, this deletion inhibits flowering function and leads plants to super early flowering. This phenomenon has been induced by introducing and expressing an antisense DNA in plants, thereby inhibiting "MPC1" protein expression (Example 2). Furthermore, the cDNA of rice-derived "Os-MPC1", which shows significant homology with said Arabidopsis cDNA, also complement the super early flowering mutation of Arabidopsis (Example 5). It is therefore thought that these proteins exist widely in plants and regulate the flowering time.

Many plants including Arabidopsis vegetatively grow for a certain period of time after germination, flower, and reproductively grow. The genes of the present invention are essential to maintain vegetative growth, and to regulate the transition from vegetative growth to reproductive growth. In other words, the expression level of this gene regulates flowering. Therefore, the flowering time of plants can be changed by artificially regulating the expression of the genes of the present invention, which leads to productivity increase of useful plants.

DNAs used in this invention are not limited to DNAs encoding Arabidopsis-derived "MPC1" or rice-derived "Os-MPC1" protein mentioned above. Other DNAs encoding proteins functionally equivalent to these proteins can also be used.

An example of these DNAs is a DNA encoding a protein having an amino acid sequence substantially identical to that of Arabidopsis-derived "MPC1" or rice-derived "Os-MPC1" protein, whose amino acid sequence is shown in SEQ ID NO: 1 or 8. "An amino acid sequence substantially identical" used herein means a sequence in which changes such as deletion, substitution, addition, and/or insertion have occurred at one or more amino acid residues of the control amino acid sequence, and an amino acid sequence constitutes a protein having flowering regulating activity as the protein comprising the control amino acid sequence. Changes such as deletion, substitution, and addition can be performed at several amino acid residues, for example, by site-directed mutagenesis (Kunkel et al. (1985), Proc. Natl. Acad. Sci. USA, vol.82: p488–). Mutations of amino acids can also occur spontaneously.

Comparing amino acid sequences of proteins having flowering regulating activity of Arabidopsis and rice, high homology is found particularly in the region comprising zinc finger motifs and the region comprising an acidic amino acid cluster at the C-terminus. A zinc finger or zinc finger structure is a structure in which a part of a protein folds chelating zinc (Zn) to construct a protruding structure like a finger, and is thought to play an important role when the protein binds to nucleic acid or other protein (Roosenfeld et al. (1993), J. Biomol. Struct. Dyn., Vol.11:p557–). An amino acid sequence that can form a zinc finger structure is called a zinc finger motif, several types of which are known. Zinc fingers of Cys2-His2 (C2H2) type are found at the amino acids 306 to 327 of the Arabidopsis-derived "MPC1" protein and the amino acids 310 to 331 of rice-derived "Os-MPC1" protein. These motifs can be identified by, for example, a program such as "MOTIF" of "GenomeNet", which is provided by Institute for Chemical Research, Kyoto University through the internet.

Acidic amino acid clusters are found in some kinds of transcription regulating proteins and sometimes play an important role in activating transcription (T. Tamura (1995), Mechanism of Transcriptional Regulation, Experimental Medicine Bioscience, Yodosha). These acidic amino acid clusters are found at amino acids 503 to 520 of Arabidopsis-derived "MPC1" protein and amino acids 488 to 505 of rice-derived "Os-MPC1" protein. These regions comprising a zinc finger motif or acidic amino acid cluster are likely to play an important role in flowering regulation of plants, and it is expected that high homology is kept in these regions of flowering regulation related proteins derived from plants other than Arabidopsis and rice.

The proteins having amino acid sequences substantially identical to that of Arabidopsis-derived "MPC1" or rice-derived "Os-MPC1" protein shown in SEQ ID NO: 1 or 8 are preferably those comprising amino acid sequences substantially identical to the regions of the above sequences comprising a zinc finger motif and a C-terminal acidic amino acid cluster.

A specific example thereof is a protein having flowering regulating activity, wherein the protein comprises amino acid sequences showing 50% or more and 60% or more homology with amino acids 278 to 348 and 465 to 607, respectively, of the amino acid sequence of SEQ ID NO: 1 (Arabidopsis), or a protein having flowering regulating activity, wherein the protein comprises amino acid sequences showing 50% or more and 60% or more homology with amino acids 282 to 352 and 450 to 592, respectively, of that of SEQ ID NO: 8 (rice).

Whether a protein has flowering regulating activity or not can be evaluated by, for example, introducing a DNA encoding said protein into super early flowering mutant plants. For example, a DNA encoding a test protein are introduced into super early flowering mutant plants such as "mpc1" Arabidopsis mutant, and expressed. The introduced DNA is judged to encode a protein having flowering regulating activity if it complements super early flowering mutant and differentiates normal stems and leaves as shown in Example 5. These DNA are thought to encode proteins having the same function as Arabidopsis-derived "MPC1" or rice-derived "Os-MPC1" protein (SEQ ID NO: 1 or 8, respectively).

In addition, other DNAs encoding proteins functionally equivalent to Arabidopsis-derived "MPC1" or rice-derived "Os-MPC1" protein can be screened by hybridization technique using the whole or a part of the DNA sequence encoding the amino acid sequence of SEQ ID NO: 1 or 8 as a probe (Southern (1975), J. Mol. Biol., vol.98: p503–; Sambrook et al. (1989), Molecular Cloning, Cold Spring Harbor Laboratory Press). Partial sequences of "MPC1" or "Os-MPC1" used as probes are at least fourteen or more nucleotide sequences. For example, GeneImage system (Amersham) can be used for hybridization. In accordance with the protocol attached to the product, test DNAs are incubated overnight with labeled probes, and those that hybridizes with the probes can be screened by washing at 50° C. with 6×SSC and 0.1% SDS. Alternatively, DNAs encoding proteins functionally equivalent to Arabidopsis-derived "MPC1" or rice-derived "Os-MPC1" protein can be isolated from other plants by PCR technique using oligonucleotides specifically hybridizing with the DNA encoding the amino acid sequence constituting "MPC1" or "Os-MPC1" protein as primers (K. Shimamoto & T. Sasaki (1995), Protocols of PCR Experiments for Plants, Cell Engineering SUPPLEMENT, Plant Cell Engineering Series 2, Shujunsha).

Flowering regulating proteins encoded by DNAs obtained by such hybridization or PCR technique are thought to have high homology with Arabidopsis-derived "MPC1" or rice-derived "Os-MPC1" protein. The term "high homology" means 45% or more, preferably 60% or more, more preferably 75% or more, still more preferably 90% or more, and most preferably 95% or more homology with at least one amino acid sequence of these proteins. The homology may possibly become 45% or less when plural amino acid residues of the amino acid sequence encoded by the isolated DNA are deleted, added, or replaced. Even in this case, the DNA can encode a protein having the region essential for the function of flowering regulating proteins and having the equivalent flowering regulating activity. As mentioned above, it is important for the protein to exhibit the flowering regulating function that high homology exists, in particular, in regions comprising a zinc finger motif region and a C-terminal acidic amino acid cluster region.

The homology between two or more genes in terms of the nucleotide sequences or the amino acid sequences of the proteins encoded by the genes can be determined using software for gene analysis, for example, DNASIS (Hitachi Software Engineering). In the software, the programs "Homology Plot," which plots homology as two-dimensional image, and "Maximum Matching," in which sequences are aligned considering gaps, are available for calculating homology between two genes (Needleman, S. B. et al. (1970), J. Mol. Biol., vol.48: p443–). The "Multialignment" program aligns three or more kinds of sequences to clarify the homologous regions (Waterman, M. S. (1986), Nucleic Acids Research, vol.14: 9095–).

Examples of plants from which the DNAs of the present invention are isolated by hybridization or PCR technique include corn, wheat, barley, rye, potato, tobacco, sugar beet, sugarcane, rape seed, soybean, sunflower, cotton, orange, grape, peach, pear, apple, Japanese apricot, tomato, Chinese cabbage, cabbage, Japanese radish, carrot, pumpkin, cucumber, melon, parsley, orchid, chrysanthemum, lily, saffron, pine, eucalyptus, acacia, poplar, Japanese cedar, Japanese cypress, bamboo, and yew, in addition to Arabidopsis and rice, but are not limited thereto. The present inventors have succeeded in isolating a flowering regulating gene encoding a protein substantially the same as Arabidopsis-derived "MPC1" or rice-derived "Os-MPC1" protein from sugar beet using hybridization or PCR technique mentioned above (Example 6).

Flowering regulating proteins of the present invention can be produced as recombinant proteins or natural proteins. Recombinant proteins can be expressed with, for example, the expression system using E. coli as a host, as fusion proteins to glutathione S-transferase (Smith, D. B. et al. (1988), Gene vol.67: p32–) or as fusion proteins with histidine-tag (Nakamura et al. (1998), Protocols of Protein Experiments for Plants, Cell Engineering SUPPLEMENT, Plant Cell Engineering Series 9, Shujunsha). The desired protein expressed as a fusion protein in *E. coli* is isloated by purifying the fusion protein by affinity chromatography with glutathione or metal ions as ligands and cutting out the desired protein by an appropriate protease treatment. Natural proteins can be produced by known methods for preparing proteins from plants (Nakamura et al. (1998), Protocols of Protein Experiments for Plants, Cell Engineering SUPPLEMENT, Plant Cell Engineering Series 9, Shujunsha).

Using recombinant or natural flowering regulating proteins prepared by the method mentioned above, polyclonal or monoclonal antibodies against them can be generated (Nakamura et al. (1998), Protocols of Protein Experiments for Plants, Cell Engineering SUPPLEMENT, Plant Cell Engineering Series 9, Shujunsha). Polyclonal antibodies can be generated by, for example, the method below. A laboratory animal such as a mouse is immunized with the prepared protein or its partial fragments mixed with appropriate adjuvant by intraperitoneal or subcutaneous injection. Additional immunization is then performed 2 to 10 times every one to four week, preferably every one or two week. After the fourth week, the blood is collected, serum is obtained to serve as antibody, and the antibody titer is measured by, for example, western blotting. The obtained antibody can be used in various experiments.

Monoclonal antibodies can be produced by fusing myeloma cells and the spleen cells obtained from the laboratory animal such as a mouse immunized by the method mentioned above and cloning the hybridoma producing the desired antibody. The hybridoma is cultivated in an appropriate medium to obtain the desired monoclonal antibody from the culture supernatant. A large amount of antibody can be obtained when hybridoma is cultivated in ascites. For example, hybridoma is transplanted into a nude mouse and allowed to grow. The monoclonal antibody produced in ascites of said animal is then collected.

Plant flowering regulation of the present invention can be performed by enhancing or inhibiting the expression of DNAs encoding the flowering regulating proteins mentioned above in target plants. Specifically, transgenic plants are generated by introducing said DNA or the antisense DNA against said DNA to the target plant. The DNA or the antisense DNA can be placed under the control of an appropriate inducible promoter to subtly regulate the degree of activation or inhibition of flowering and flowering time.

These DNAs can be expressed by introducing, into plant cells, a recombinant double-stranded DNA molecule comprising an expression cassette comprising (i) a promoter that is transcribed in plant cells, (ii) the whole or a part of the DNA encoding a flowering regulating protein of the present invention fused at the downstream of the promoter in sense or antisense direction, and if necessary, (iii) a terminator sequence fused at the downstream of the DNA, which comprises a polyadenylation site essential for stabilizing the transcript. "A part of the DNA encoding a flowering regulating protein" used herein means a part of the DNA encoding a complete flowering regulating protein that regulates flowering when it is expressed in plant cells. The present invention includes these recombinant double-stranded DNA molecules. The recombinant double-stranded DNA molecules can have DNA sequences essential to transfer the molecule to host plant cells or to maintain it in the host cells at its 5'- and/or 3'-end as well as constituent elements described above.

An expression cassette can comprise a promoter to express constitutively or inducibly the DNA encoding the inserted flowering regulating protein of the present invention. Examples of promoters for constitutive expression are 35 S promoter of cauliflower mosaic virus (Odell et al. (1985), Nature, vol.313: p810–) and rice actin promoter (Zhang et al. (1991), Plant Cell, vol.3: p1155–). Examples of promoters for inducible expression are promoters known to express by external factors such as infection or invasion of fungi, bacteria, or virus, low or high temperature, dryness, irradiation of ultraviolet rays, contacting with specific compounds. Examples of these promoters are rice chitinase gene promoter (Xu et al. (1996), Plant Mol. Biol., vol.30: p387–) and tobacco PR protein gene promoter (Ohshima et al. (1990), Plant Cell, vol2: p95–), both of which are induced by infection or invasion of fungi, bacteria, or virus, rice "lip19" gene promoter that is induced by low temperature (Aguan et al. (1993), Mol. Gen. Genet., vol.240: p1–), Arabidopsis "HSP18.2" gene promoter that is induced by high temperature (Yoshida et al. (1995), Appl. Microbiol. Biotechnol., vol.44(3–4): p466–), rice "rab" gene promoter that is induced by dryness (Yamaguchi-Shinozaki et al. (1990), Plant Mol. Biol., vol.14(1): p29–), parsley chalcone synthase gene promoter that is induced by ultraviolet rays (Schulze-Lefert et al. (1989), EMBO J., vol.8: p651–), and corn alcohol dehydrogenase gene promoter that is induced under anaerobic conditions (Walker et al. (1987), Proc. Natl. Acad. Sci. USA vol.84: p6624–). Besides, rice chitinase gene promoter and tobacco PR protein gene promoter are induced by specific compound such as salicylic acid, and rice "rab" gene promoter by sprinkling of a plant hormone abscisic acid.

Various cloning vectors comprising the replication origin of *E. coli* and a marker gene for screening transformed bacterial cells are available to introduce the recombinant DNA molecules into plants. Examples of these vectors include pBR322, pUC series, and M13mp series. A desired sequence can be introduced into a vector at an appropriate restriction enzyme site. A plasmid DNA obtained can be characterized by restriction endonuclease cleavage site analysis, gel electrophoresis, and other biochemical-molecular biological methods. Once the plasmid DNA is prepared, it can be cleaved and ligated with another DNA. The sequence of the plasmid DNA can be cloned into the same plasmid or other plasmids.

When the whole of a DNA encoding a flowering regulating protein of the present invention, for example, the whole region of Arabidopsis-derived "MPC1" cDNA, shown in SEQ ID NO: 2, is ligated at the downstream of a promoter in sense direction, expression of the flowering regulating gene can be expressed constitutively or inducibly depending on the property of the promoter used. Then, the activity of the flowering regulating protein in plant cells constitutively or inducibly increases, and consequently, delay or inhibition of flowering can constitutively or inducibly is caused in plants.

When the whole or a part of a DNA encoding a flowering regulating protein, for example, the whole or a part region of Arabidopsis-derived "MPC1" cDNA, shown in SEQ ID NO: 2, is ligated at the downstream of a promoter mentioned above in antisense direction, the antisense RNA complementary to the transcript of "MPC1" cDNA can be constitutively or inducibly expressed depending on the property of the promoter used. The expression of a flowering regulating protein of the present invention is constitutively or inducibly inhibited in plant cells, and consequently, flowering can be enhanced constitutively or inducibly in plants. Antisense DNAs used do not have to encode the antisense RNAs completely complementary to the transcript of endogenous flowering regulating protein gene as long as it can inhibit the expression of endogenous flowering regulating protein.

In plants, when a gene is ligated in sense direction at the downstream of a promoter causing constitutive and strong expression, the expression of both of the gene introduced and the corresponding endogenous gene is sometimes inhibited (Montgomery (1998), Trends Genet., 14, 255–). This phenomenon is called co-suppression. When a flowering regulating gene of the present invention, for example, the whole region of Arabidopsis-derived "MPC1" cDNA, shown in SEQ ID NO: 2, is ligated in sense direction at the downstream of 35 S promoter, the expression of the endogenous flowering regulating protein in plant cells can be inhibited by co-suppression to enhance flowering in plants.

Moreover, when a part of a DNA encoding a flowering regulating protein of the present invention, for example, a part region of "MPC1" cDNA, shown in SEQ ID NO: 2, is ligated at the downstream of a promoter mentioned above in sense direction, an incomplete flowering regulating protein can be constitutively or inducibly expressed depending on the property of the promoter used. The incomplete flowering regulating protein that constitutively or inducibly accumulates in cells can inhibit the normal function of the flowering regulating protein, thereby enhancing flowering constitutively or inducibly in plants.

Both dicotyledon and monocotyledon can be used at target plants for generating plants whose flowering behavior is changed in comparison with wild type plants. Particularly important plants are grain (for example, rye, wheat, corn, barley, and rice), fruits (for example, orange, grope, peach, pear, apple, and Japanese apricot), vegetables (for example, tomato, Chinese cabbage, cabbage, Japanese radish, carrot, pumpkin, potato, cucumber, melon, and parsley), ornamental plants (for example, orchid, chrysanthemum, lily, and saffron), other industrial crops of economical importance (for example, tobacco, sugar beet, rape seed, soybean, sunflower, and cotton), and trees that require a long period till flowering (for example, eucalyptus, acacia, and poplar, which are used as wood pulp, and cedar, Japanese cypress, pine, bamboo, and yew, which are used as lumber).

Various methods can be used for introducing expression cassettes into plant host cells. Examples thereof are transformation of plants cells with T-DNA using *Agrobacterium tumefaciens* or *Agrobacterium rhizogenes* as a transformation mediator, direct introduction into protoplast (infection method, electroporation method, etc.), and particle gun method, but are not limited thereto.

Direct introduction into protoplast needs no special vectors. For example, simple plasmids such as pUC derivatives can be used. Some methods for introducing a desired gene into plant cells need other DNA sequences. For example, when a Ti or Ri plasmid is used to transform plant cells, at least right side sequence or usually both side sequences at the T-DNA region of Ti or Ri plasmid should be connected adjacent to a gene to be introduced.

When Agrobacterium is used to transform plant cells, an expression cassette to be introduced should be cloned in a special plasmid, an intermediate vector or binary vector. An intermediate vector is not replicated in Agrobacterium. An intermediate vector is transferred into Agrobacterium with a helper plasmid or by electroporation. Having regions homologous to T-DNA sequence, an intermediate vector is integrated into Ti or Ri plasmid of Agrobacterium by homologous recombination. Agrobacterium used as a host has to comprise vir region. Usually, Ti or Ri plasmid comprises vir region and can transfer T-DNA into plant cells by its function.

In contrast, since a binary vector can be replicated and maintained in Agrobacterium, if it is introduced into Agrobacterium with a helper plasmid or by electroporation, T-DNA on a binary vector can be transferred into plant cells by the function or vir region of the host. The present invention also includes intermediate vectors or binary vectors thus obtained, and microorganisms such as *E. coli* or Agrobacterium comprising them.

Transformed plant cells can be regenerated to a plant. The method for regeneration depends on the kind of the plant cells. Examples thereof are the methods of Fujimura et al. (Fujimura et al. (1995), Plant Tissue Culture Lett., vol.2: p74–) for rice, Shillito et al. (Shillito et al. (1989), Bio/Technology, vol.7: p581–) for corn, Visser et al. (Visser et al. (1989), Theor. Appl. Genet., vol.78: p594–) for potato, and Akama et al. (Akama et al. (1992), Plant Cell Rep., vol.12: p7–) for Arabidopsis. In plants generated by these methods or plants obtained from their vehicles for reproduction (for example, seeds, tubers, cuttings), the flowering regulating protein expression of the present invention changes in comparison with wild type plants, which changes the flowering behavior. The present invention includes transgenic plants thus obtained.

The present invention provides a novel gene that inhibits flowering of plants. When this gene is introduced into other plants and expressed in the plants, it can inhibits or enhance flowering of the plants.

Various cultivars of grain and vegetable that matures earlir or later than usual can be generated by regulating flowering, which produces such as agriculturally important value as expansion of the suitable cultivation place, increase of yield, and supply of crops with high value added. In particular, though the deterioration of quality by bolting and flowering is a problem in leaf and stem vegetables such as Chinese cabbage and root vegetables such as Japanese radish, the type of cultivation is limited at present. Therefore, flowering inhibition will bring a great effect such as the expansion of the cultivation season and the suitable cultivation place. Arbitrary flowering regulation will also be considerably useful if it is applied to a cultivar having superior characteristics such as good taste or strong disease resistance. Furthermore, enhancing the floral budding of fruits will increase their productivity or change the flowering time, which enables the production and shipment of fruits out of season. In addition, inhibiting flowering of wood will not only enhance alternation of generations by shortening the period required for flowering but also enhance vegetative growth or suppress allergy induction in humans caused by scatter of pollen, which is economically and socially significant.

The present invention is illustrated in detail below with reference to Examples, but is not to be construed as being limited thereto. Besides, methods for general gene recombination such as cleavage and ligation of DNAs, transformation of *E. coli*, determination of nucleotide sequences of genes, hybridization were performed, unless otherwise mentioned, based on manuals attached to commercial reagents and apparatus or laboratory books, for example, "Molecular Cloning" (Sambrook et al. (1989), Cold Spring Harbor Laboratory Press). In addition, cultivation of Arabidopsis using agar medium or soil, mating manipulation, preparation of genomic DNAs, genetic analysis are performed, unless otherwise mentioned, in accordance with laboratory books, for example, "Experimental Protocols for Model Plants" (Shimamoto & Okada (1996), Cell Engineering SUPPLEMENT, Plant Cell Engineering Series 4, Shujunsha).

EXAMPLE 1

Isolating Arabidopsis Flowering Regulating Gene "MPC1"

In order to clone a flowering regulation gene from Arabidopsis, mutants that flower immediately after cotyledon expansion (super early flowering mutants) was isolated as follows. The M2 (seeds after self-fertilization of individuals obtained by sowing mutagenized seeds) of Arabidopsis (ecotype: Landsberg) mutagenized with chemical mutagen EMS were prepared and sown on agar medium (1/2 B5 medium (Gamborg et al. (1968), Exp. Cell Res., vol.50: p151–); 1% sucrose, 0.8% agar). The screening was performed by observing the morphology of seedlings germinated. About fifty thousand individuals divided into ten lots were screened to obtain one kind of super early flowering mutant. This mutant was named "mpc1." Since "mpc1" flowers before the plant sufficiently matures, its flower has no fertility and the strain cannot be maintained. Five thousand individuals from the lot in which the mutant had been obtained were cultivated to obtain seeds (M3) of each individual. Strains of heterozygotes that segregate the super early flowering mutant were obtained by sowing these seeds individually and observing their seedling. The "mpc1" mutation was found to be caused by single recessive gene from the facts that the mutation segregates the mutant individuals in the proportion of one fourth in the M3 generation and also segregates the mutant individuals in the proportion of one fourth in the F2 generation obtained by mating with the wild type.

The strains of heterozygotes were backcrossed onto wild type strain Landsberg two times and the next generation obtained was mated with wild type strain Columbia. A DNA was extracted from each individual of the F2 generation by the conventional methods and analyzed for the recombinant value between the mutant characteristics and RFLP (Restriction Fragment Length Polymorphism) marker (Liu et al. (1996), Plant J., vol.10(4):p733–), CAPS (Co-dominant cleaved Amplified Polymorphism Sequences) marker (Konienczny et al. (1993), Plant J., vol.4:p403–), and microsatelite marker (Bell et al. (1994), Genomics, vol.19:p137–) to map the gene causing the mutation on a chromosome. The desired gene was mapped between well-known DNA markers on the chromosome 5, mi2 (Lister & Dean (1995), Weeds World, vol.2(I):p23–, and Ds389-14 (Smith et al. (1996), Plant J., vol.10(4):p721–).

In order to isolate DNA fragments covering this chromosome region, CIC-YAC library (Creusot et al. (1995), Plant J., vol.8: p763–), P1 library (Liu et al. (1995), Plant J., vol.7: p351–) and TAC library (Liu et al. (1995), The Molecular Biology Society of Japan 18th Annual Meeting) were screened with the two marker mentioned above and DNA clones were obtained. DNA fragments were prepared from the clones obtained, novel DNA markers were generated, and detailed chromosome mapping of genes and screening of DNA clones were repeated on after another. As a result, the desired gene was found to locate between the markers 16EB53 and Z11-1, which can be obtained from the genomic DNA by PCR amplification. 16EB53 can be obtained by PCR with synthetic oligonucleotide primers "GGATC-CGAAC CCGACTCGGT ACC" (SEQ ID NO: 4) and "GCTTATGGAT GTGGACTCTC TAAC" (SEQ ID NO: 5), and Z11-1 can be obtained by PCR with synthetic oligonucleotide primers "AGGTCCTACA ACTACAACAG TT" (SEQ ID NO: 6) and "GAGGAAGCTA GTATTCTCTT TG" (SEQ ID NO: 7).

The chromosome region between the markers 16EB53 and Z11-1 is indicated with DNA contigs of four kinds of TAC clones (11K22, 22K2, 19A20, and 20I12) shown in FIG. 1. These TAC clones are about 70 to 100 kb long. When each of these clones was introduced into the mutant individual through Agrobacterium tumefaciens, the introduction of the three clones other than 20I12 reverted to wild-type (methods for gene introduction and cultivation of transformed plants are described in detail in Example 2). When cDNA library of Arabidopsis (Newman et al. (1994), Plant Physiol., vol.106: p1241–) was screened using about 50 kb region common to these three clones as a probe, six kinds of gene cDNAs were obtained. The sites of these genes were mapped on DNA contigs. Moreover, the clones were completely or partially digested with restriction enzymes and subcloned to confirm whether each gene contributed to reversion. As a result of introducing these subclones, one gene having reversion ability was identified. This gene was confirmed to be the gene causing the super early flowering mutation "mpc1," that is, flowering regulating gene "MPC1". Analysis of this genomic region and the nucleotide sequence of the cDNA clones clarified that "MPC1" structural gene has 22 exons divided by 21 introns and that the length is 5580 bp. The protein encoded by the gene has a molecular weight of 69.5 kDa with 611 amino acid residues. It contains a C2H2 type zinc finger (Rosenfeld et al. (1993), J. Biomol. Struct. Dyn., vol.11: p557), which is characteristic of nucleic acid binding proteins, and an acidic amino acid cluster, in transcription activating domain of a transcription factor at amino acids 306 to 327 and 503 to 520, respectively, of SEQ ID NO: 1.

Homology search using DDBJ/EMBL/GenBank database detected sequences having partial homology, but each of them was a fragmentary sequence with unknown function. Specifically, they are a partial cDNA sequence of rice (EST C72616) and a genomic primary structure sequence of Arabidopsis (Z97342). This homologous sequence of Arabidopsis is located on the chromosome different from "MPC1" gene of the present invention and is greatly different from "MPC1" gene in that the region corresponding to that between the fifth and tenth exon of "MPC1" gene is missing. The sequence may be derived from the gene of the present invention by deletion of the above region, and thus be originally a gene related to flowering. These results indicates that genes homologous to that of the present invention with specific function have not been found so far and therefore the gene of the present invention is novel. In addition, the analysis of the nucleotide sequence of this gene of the "mpc1" mutant revealed that guanine base at 5039 of SEQ ID NO: 3 is replaced with adenine and that a termination codon occurs in the coding frame. An incomplete protein lacking amino acids from 541 and the following C-terminal region of "MPC1" protein by the base substitution is thought to be expressed in "mpc1" mutant. Since this protein lacks flowering regulating function partially or completely, it is thought that the plant cannot maintain vegetative growth and causes super early flowering.

EXAMPLE 2

Inducing Flowering by Gene Introduction

An antisense gene was constructed using a part of the Arabidopsis flowering regulating gene "MPC1" cDNA. The sequence between the BamHI site at nucleotide 1650 and the SphI site at 1984 of cDNA shown in SEQ ID NO: 2 was separated by restriction enzyme digestion. To transcribe the complementary sequence of the transcript of the resulting fragment, binary vector pBI121 (Jefferson et al. (1987), EMBO J., vol.6: p3901–) was cleaved at the XbaI site at the downstream of 35 S promoter, blunted, cleaved with BamHI, and ligated with the fragment obtained above that had been cleaved with SphI, blunted, and cleaved again with BamHI. This construct was used as an antisense gene.

The antisense gene was introduced into Arabidopsis by a gene transfer method using *Agrobacterium tumefaciens*. First, the antisense gene expression vector mentioned above was transferred into *Agrobacterium tumefaciens* by electroporation. The expression vector has the kanamycin resistance gene as the marker. The antisense gene expression vector DNA was mixed with *Agrobacterium tumefaciens* suspended in 10% glycerol and the mixture had electric pulse added in a 1 mm wide cuvette electrodes with a setting of 25 µF, 600 Ω, and 1.8 kV. The cells were then cultivated on LB agar medium (1% bactotryptone, 0.5% yeast extract, 0.5% sodium chloride, 1.2% bactoagar) supplemented with 25 µg/ml kanamycin and 50 µg/ml refampicin at 28° c. for two days and colonies of kanamycin resistant *Agrobacterium tumefaciens* were screened. *Agrobacterium tumefaciens* having this antisense gene was cultivated in LB liquid medium (1% bactotryptone, 0.5% yeast extract, 0.5% sodium chloride) supplemented with 50 µg/ml rifampicin and 25 µg/ml kanamycin at 28° C. for 16 hours to prepare culture of *Agrobacterium tumefaciens*.

Seeds of Arabidopsis sterilized with 1% sodium hypochlorite were sowed in MS agar medium (Murashige & Skoog (1962), Physiol. Plant, vol.15: p473–) supplemented with 1% sucrose and 0.4% Gellan Gum, and grown at 25° C. for 14 days. A hypocotyl of grown Arabidopsis was cut out and put on CIM medium (B5 agar medium (Gamborg et al. (1968), Exp. Cell Res., vol.50: p151–) supplemented with 0.5 mg/l 2,4D, 0.05 mg/l kinetin, 2% glucose, and 0.4% Gellan Gum), and cultivated at 25° C. for 6 days in the dark.

This hypocotyl was mixed with the above culture of *Agrobacterium tumefaciens* having the antisense gene, put on CIM medium again and cultivated at 25° C. for two days to infect the hypocotyl with the bacteria. The hypocotyl was sterilized by washing in B5 liquid medium comprising 150 mg/l Claforan (cefotaxime sodium) and 2% glucose for five hours with shaking. The resulting hypocotyl was subcultured in SIM medium (B5 agar medium containing 2 mg/l gelatin, 0.2 mg/l IBA, 150 mg/l Claforan, 50 µg/ml kanamycin, 2% glucose, and 0.4% Gellan Gum) every week to differentiate and screen the transformant. 35 S promoter, which promotes to express the antisense gene, is known as a constitutive expression promoter. Pistils were differentiated directly from the hypocotyl in fourth week of subcultivation.

EXAMPLE 3

Isolating Rice Flowering Regulating Gene "Os-MPC1"

Homology search of DDBJ/EMBL/GenBank database with the sequence of Arabidopsis flowering regulating gene "MPC1" as the probe detected a partial cDNA sequence of rice (EST C72616) that is partially homologous to MPC1. The whole cDNA sequence of this gene, whose function was unknown, was isolated as follows. First, cDNA library derived from rice immature seeds was screened using the partial cDNA sequence on the database as the hybridization probe and one kind of cDNA clone was obtained. The cDNA of the clone was found to be 2248 bp long by nucleotide sequence determination and the protein encoded by this cDNA has a molecular weight of 68.6 kDa with 604 amino acid residues. The nucleotide sequence of the cDNA and the amino acid sequence of the protein encoded by the cDNA are shown in SEQ ID NO: 9 and 8, respectively. The sequence identity between the amino acid sequence of this protein and that of Arabidopsis "MPC1" protein is 61%, which is significant homology. Therefore, this gene was thought to be the gene corresponding to Arabidopsis "MPC1" in rice and was named "Os-MPC1." "Os-MPC1" protein was found to have a zinc finger motif and an acidic amino acid cluster as "MPC1" at amino acids 310 to 331 and 488 to 505, respectively, of SEQ ID NO: 8.

EXAMPLE 4

Chromosome Mapping of Rice "Os-MPC1" Gene

Chromosomal DNA fragments derived from a part of 3' region of "Os-MPC1" gene were amplified from rice strains "Asominori" and "IR24" by PCR. Synthetic oligonucleotide primers "GACGAGAAAC TTATTATGCA TATG" (SEQ ID NO: 10) and "GGTCTTGATA CTGCTCTACA GTTATG" (SEQ ID NO: 11) were used for amplification. About 1.3 kb amplified gene fragments thus obtained showed restriction fragment length polymorphism (RFLP); cleavage patterns were different between strains of "Asominori" and "IR24" when digested with restriction enzyme SspI. The locus of "Os-MPC1" gene on a chromosome can be determined by correlating this RFLP with the RFLP map already known for rice. The locus of "Os-MPC1" was determined by calculating recombination value between "Os-MPC1" gene fragments and RFLP markers whose sites have been already determined using the chromosomal DNA of Recombinant Inbred (RI) strains generated from plants obtained by mating between rice "Asominori" and "IR24" (Tsunematsu et al. (1993), Rice Genetics Newsletter, vol.10: p89–). The result of the analysis revealed that "Os-MPC1" gene was located near the well-known C152 marker at the terminus of rice chromosome 9. Any flowering regulating genes have never been found at the terminus of the chromosome 9 of rice. From this fact, "Os-MPC1" gene is a novel and fundamental flowering regulating gene, which was difficult to be detected by conventional techniques.

EXAMPLE 5

Complementing Arabidopsis Super Early Flowering Mutation by Rice "Os-MPC1" Gene

Flowering regulating function of rice "Os-MPC1" gene isolated was tested. "Os-MPC1" cDNA was first cleaved at the NotI site at the 3'-terminal connection with the vector, blunted, and then cleaved at the NheI site in the 5' noncoding region to obtain only the cDNA sequence without the vector sequence. Separately, binary vector pBI121 (Jefferson et al. (1987), EMBO J., vol.6: p3901–) was cleaved at the SmaI site at the downstream of 35 S promoter and ligated with the blunted 3'-end of the above-mentioned cDNA fragment. The ligation product was then cleaved at the XbaI site at the upstream of the SmaI site in the vector, ligated at this site with the NheI site of the cDNA fragment to obtain the expression vector of "Os-MPC1" gene. The "Os-MPC1" gene was introduced into the mutant by introducing the above vector into *Agrobacterium tumefaciens* and infecting the slice of root of the Arabidopsis super early flowering mutant with the bacteria (methods for gene introduction and cultivation of plants into which the mutation was introduced are described in detail in Example 2). When a root of the super early flowering mutant without the "Os-MPC1" gene was cultivated to allow it to differentiate to an individual, only the direct floral differentiation due to the influence of the mutation was observed. In contrast, it was confirmed when "Os-MPC1" gene was introduced into the mutant that the mutation was complemented and stems and leaves were differentiated and grew.

These results indicate that not only "Os-MPC1" gene is functionally proved to be a flowering regulating gene of rice but also "flowering regulating gene" of the present invention functions similarly in wide-ranging species of plants.

EXAMPLE 6

Isolating Flowering Regulating Genes from Various Kinds of Plants

The amino acid sequences encoded by Arabidopsis "MPC1" gene and rice "Os-MPC1" gene were compared with each other and two regions were selected from similar amino acid sequences commonly found in both flowering regulating proteins. Specifically, one region is "Lys Arg Gln Phe Phe His Ser" (SEQ ID NO: 12) at amino acids 484 to 490 of SEQ ID NO: 1 and the other is "Trp Ala Cys Glu Ala Phe" (SEQ ID NO: 13) at amino acids 558 to 563 of SEQ ID NO: 1. Next, four kinds of synthetic oligonucleotide primers KR1 "AAGCGGCAAT TTTAYCAYTC" (SEQ ID NO: 14), KR2 "AAGCGGCAGT TCTAYCAYTC" (SEQ ID NO: 15), KR3 "AAGCGGCAGT TCTAYCAYAG" (SEQ ID NO: 16), and KR4 "AAGCGGCAAT TTTAYCAYAG" (SEQ ID NO: 17) were prepared based on the amino acid sequence of SEQ ID NO: 12, and two kinds of synthetic oligonucleotide primers WA1 "AATACCTCAC ANGCCCA" (SEQ ID NO: 18) and WA2 "AATACTTCGC ANGCCCA" (SEQ ID NO: 19) were prepared based on the amino acid sequence of SEQ ID NO: 13.

PCR was performed using eight kinds of combinations of the primers KR1, KR2, KR3, and KR4 with the primers WA1 and WA2 and chromosomal DNA of rice (ecotype: Nipponbare) and sugar beet (ecotype: Sugarman Gold) as templates. The nucleotide sequence of each amplified fragments was determined and compared to the known flowering regulating genes.

As a result, the 1216 bp fragment of sugar beet amplified by PCR using the primers KR1 and WA2 was proved to be a part of sugar beet flowering regulating gene. The nucleotide sequence of this sugar beet gene fragment is shown in SEQ ID NO: 20. In the gene fragment, nucleotide sequence encoding amino acids are divided by three introns and their locations are the same as that of Arabidopsis "MPC1" gene.

The fragment amplified for rice by PCR using the primers KR2 and WA2 was proved to be a part of rice flowering regulating gene "OS-MPC1."

Using these amplified gene fragments, the full-length of the gene can be readily cloned by screening library clones, PCR technique, or other methods.

It is possible to obtain flowering regulating genes from not only rice and sugar beet but also various species of plants using the method mentioned above.

What is claimed is:

1. An isolated DNA encoding a protein that inhibits the transition from vegetative growth to reproductive growth in a plant transformed therewith, wherein said DNA is selected from the group consisting of:

i. a DNA encoding a protein comprising the amino acid sequence of SEQ ID NO: 1; and ii. a DNA encoding a protein having at least 61% identity to SEQ ID NO: 1 and comprises a zinc finger motif and a C-terminal amino acid cluster.

2. The DNA of claim 1, wherein said DNA comprises bases 310–2145 of SEQ ID NO: 2.

3. An expression cassette comprising the DNA of claim 1 and i a promoter that can direct transcription in plant cells, and ii a signal involved in transcription termination of RNA molecules and polyadenylation, wherein the signal functions in plants, and wherein said DNA is fused to said promoter in sense or antisense direction.

4. A transgenic plant cell comprising the expression cassette according to claim 3.

5. A method for producing a protein that inhibits the transition from vegetative growth to reproductive growth in a plant transformed therewith comprising (a) cultivating the plant cell according to claim 4 under conditions wherein the protein encoded by said DNA is expressed, and wherein said DNA is fused to said promoter in the sense direction, and (b) recovering the protein encoded by said DNA from said transgenic plant cell.

6. A transgenic plant comprising the plant cell according to claim 4.

7. A method for producing a transgenic plant, comprising (a) introducing the expression cassette according to claim 3 into a plant cell and (b) regenerating a transgenic plant from said plant cell.

8. An isolated DNA encoding an antisense RNA complementary to a transcription product of the DNA of claim 1.

9. A method for inhibiting the transition from vegetative growth to reproductive growth of a plant, comprising introducing the DNA according to claim 1 into a plant, wherein expression of said DNA results in inhibition of the transition from vegetative growth to reproductive growth of said plant.

10. A method for accelerating the flowering time of a plant, comprising introducing the DNA of claim 8 into a plant, wherein expression of said DNA results in acceleration of the flowering time.

* * * * *

UNITED STATES PATENT AND TRADEMARK OFFICE
CERTIFICATE OF CORRECTION

PATENT NO.    : 6,630,616 B1
DATED         : October 7, 2003
INVENTOR(S)   : Nobumasa Yoshida et al.

It is certified that error appears in the above-identified patent and that said Letters Patent is hereby corrected as shown below:

<u>Title page, Item [54] and Column 1, line 1,</u>
Title is corrected to read -- THE ARABIDOPSIS MPCI GENE AND METHODS FOR CONTROLLING FLOWERING TIME --

<u>Title page,</u>
Item [56], References Cited, OTHER PUBLICATIONS:
"Fisher et al." reference, "pp. 1566-1570" is changed to -- pp. 1565-1570 --
"Aukerman, MJ et al." reference, "Aukeman" is changed to -- Aukerman --
"Yang et al". reference, "Development Biology" is changed to -- Developmental Biology --
"Zhang et al." reference, "Rice Plant" is changed to -- Rice Plants --
"Gamborg et al." reference, "Cultures in" is changed to -- Cultures of --
"Gamborg et al." reference, "Experimenal" is changed to -- Experimental --
"Creusot et al." reference, *"Arabisopsis"* is changed to -- *Arabidopsis* --

Signed and Sealed this

Eleventh Day of May, 2004

JON W. DUDAS
*Acting Director of the United States Patent and Trademark Office*